United States Patent [19]

Renaut et al.

[11] Patent Number: 5,637,613
[45] Date of Patent: Jun. 10, 1997

[54] 15-DEOXYSPERGUALIN ANALOGS, THEIR METHOD OF PREPARATION AND THEIR USE IN THERAPEUTICS

[75] Inventors: Patrice Renaut, Hauteville-lès-Dijon; Luc Lebreton, Dijon; Patrick Dutartre, Longchamp; Soth Samreth, Longvic; Catherine Derrepas, Talant; Jean M. Rognon, Morteau, all of France

[73] Assignee: Fournier Industrie et Sante, France

[21] Appl. No.: 393,330

[22] Filed: Feb. 23, 1995

[30] Foreign Application Priority Data

Feb. 24, 1994 [FR] France .................................. 94 02125
Jun. 1, 1994 [FR] France .................................. 94 06706

[51] Int. Cl.$^6$ ..................... A61K 31/24; C07C 271/06; C07C 237/04
[52] U.S. Cl. ..................... 514/540; 514/588; 514/619; 514/626; 560/33; 564/59; 564/160; 564/161; 564/192; 564/201; 564/209
[58] Field of Search ..................... 560/33; 564/160, 564/192, 59, 201, 209, 161; 514/534, 540, 588, 619, 626

[56] References Cited

FOREIGN PATENT DOCUMENTS 105193 4/1984 European Pat. Off. .
181592 5/1986 European Pat. Off. .

OTHER PUBLICATIONS

Int. J. Immunopharmac., vol. 14, No. 4, 1992, pp. 731–737, H. Fuji et al., "Deoxyspergualin, a novel immunosuppressant, markedly inhibits human mixed lymphocyte reaction and cyctotoxic T-lymphocyte activity in vitro".

Journal of Medicinal Chemistry, vol. 35, No. 4, 1992, Washington U.S., pp. 724–734, J. R. Lakanen et al., "Alpha–Methyl polyamines: metabolically stable spermidine and permine mimics capable of supporting growth in cells depleted of polyamines".

Journal of Antibiotics, vol. 41, No. 2, 1988, Tokyo, Japan, pp. 234–238, H. Karamochi et al., "The antiproliferative action of action of deoxyspergualin is different from that induced by amine oxidase".

Journal of Antibiotics, vol. 41, No. 11, Nov. 1988, Tokyo, Japan, pp. 1629–1643, R. Nishizawa et al., "Synthesis and Biological Activity of Spergualin Analogues".

*Primary Examiner*—Joseph Conrad
*Attorney, Agent, or Firm*—Ostrolenk, Faber, Gerb & Soffen, LLP

[57] ABSTRACT

The present invention relates, by way of novel industrial products, to compounds which are structurally related to 15-deoxyspergualin and which have the formula $$H_2N-\underset{NH}{\overset{NH}{\underset{\|}{C}}}-NH-(CH_2)_n-NH-\underset{\|}{\overset{O}{C}}-A-\underset{\|}{\overset{O}{C}}-NH-(CH_2)_4-NH-(CH_2)_2-\underset{\underset{CH_3}{|}}{\overset{*}{C}H}-NH_2 \quad (I)$$

in which:

A is a single bond, a group —CH$_2$—, a group —CH$_2$O—, a group —CH$_2$NH—, a group —CH(OH)—, a group —CHF— or a group —CH(OCH$_3$)—, and n is equal to 6 or 8, and their addition salts.

These novel compounds are useful especially as immunosuppressants. The invention further relates to the method of preparing said compounds.

13 Claims, No Drawings

15-DEOXYSPERGUALIN ANALOGS, THEIR METHOD OF PREPARATION AND THEIR USE IN THERAPEUTICS

FIELD OF THE INVENTION

The present invention relates to novel compounds which are structurally related to 15-deoxyspergualin. It further relates to their method of preparation and to their use in therapeutics, especially as immunosuppressants.

PRIOR ART

15-Deoxyspergualin, which was initially studied for its antitumoral activity, is known to possess a good activity in the field of immunosuppression. Numerous publications refer to this activity, especially: "Deoxyspergualin in lethal murine graft-versus-host disease", Transplantation, vol. 51, 712–715, no. 3 (March 1991), and "15-Deoxyspergualin: From Cytostasis to Immunosuppression", Behring Inst. Mitt., no. 82, 231–239 (1988).

However, 15-deoxyspergualin does not have a satisfactory chemical stability and attempts have been made to obtain more stable derivatives, for example by replacing the α-hydroxyglycine residue of 15-deoxyspergualin with various α- or ω-amino acids or by modifying the chain segment carrying the guanidine group. For examples of such modifications, reference may be made to EP-A-0 181 592 or EP-A-0 105 193.

SUBJECT OF THE INVENTION

The present invention proposes novel products whose general structure is still related to that of 15-deoxyspergualin, which are chemically stable and which have a greater immunosuppressive activity than the known products of the prior art.

The notable differences in chemical structure between the products according to the invention and the known products of the prior art are the inversion of the amide bond linking the guanidinohexyl residue to the central chain segment of the molecule, the nature of the central chain segment and the introduction of a branched chain containing a chiral center into the spermidine part of the molecule.

The 15-deoxyspergualin-analogous compounds according to the invention are selected from the group consisting of:

(i) the compounds of the formula

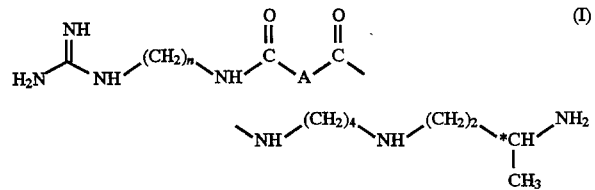

(I)

in which:

A is a single bond, a group —CH$_2$—, a group —CH$_2$O—, a group —CH$_2$NH—, a group —CH(OH)—, a group —CHF— or a group —CH(OCH$_3$)—, and n is equal to 6 or 8; and (ii) their addition salts.

In formula I and the other formulae (i.e. II, IV, VI, XI, XI' and XII) which follow, *C is an asymmetric carbon atom (alternative nomenclature: "chiral carbon atom").

According to the invention, a method of preparing the compounds of formula I and their addition salts is also proposed, said method comprising the deprotection of a compound of the formula

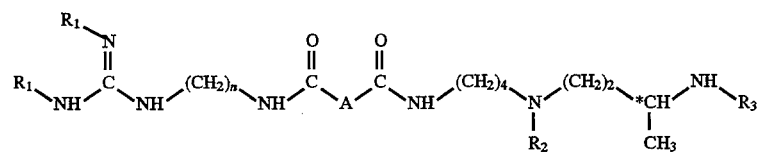

(II)

in which:

A and n are defined as indicated above, and

R$_1$, R$_2$ and R$_3$, which are identical or different, are each a protecting group for the amine group, by one or more reaction treatments known to those skilled in the art, in order to replace all the groups R$_1$, R$_2$ and R$_3$ with a hydrogen atom.

The use of a substance selected from the compounds of formula I and their non-toxic addition salts is also proposed for the preparation of a drug intended for use in therapeutics to combat immune disorders, or to combat malaria, or else as a pharmacological reagent.

DETAILED DESCRIPTION OF THE INVENTION

Addition salts are understood as meaning the acid addition salts obtained by reacting a mineral acid or an organic acid with a compound of formula I. The preferred mineral acids for salification are hydrochloric, hydrobromic, sulfuric and phosphoric acids. The preferred organic acids for salification are fumaric, maleic, methanesulfonic, oxalic, citric and trifluoroacetic acids.

In view of the presence of the asymmetric carbon atom, denoted by *C above, and the nature of the group A, the compounds of formula I can have one or two chiral carbon atoms. When A is —CH$_2$—, —CH$_2$O— or —CH$_2$NH—, the present invention encompasses among the compounds of formula I the racemates, where *C has the (R,S) configuration, and the enantiomers, where *C has the (R) or (S) configuration. When A is —CH(OH)—, —CHF— or —CH(OCH$_3$)—, the present invention encompasses among the compounds of formula I, which then have two chiral sites, the substantially equimolecular mixture of the four diastereoisomers, the "hemiracemates" (R,S)—A—(R)—*C, (R,S)—A—(S)—*C, (R)—A—(S,R)—*C and (S)—A—(S,R)—*C, and each of the four diastereoisomers.

In practical terms, the asymmetric carbon atom denoted by *C preferably has the (R,S) or (R) configuration.

The compounds of formula I can be prepared by methods known per se by applying conventional reaction mechanisms, such as the formation of an amide bond, and especially by applying the methods of peptide chemistry.

As indicated above, the method of preparation which is proposed according to the invention comprises the deprotection of a compound of formula II.

In practical terms, the protecting groups $R_1$, $R_2$ and $R_3$ which are to be replaced with a hydrogen atom will be amino-protecting groups of a type known in the field of peptide chemistry for temporarily blocking "amine" groups which are not totally substituted.

The following can be used among the groups, which are suitable for this purpose:

(α) groups of the oxycarbonyl type, for example alkoxycarbonyl and benzyloxycarbonyl groups:
Boc: t-butoxycarbonyl [or (1,1-dimethylethoxy) carbonyl],
Fmoc: 9-fluorenylmethoxycarbonyl,
Foc: furfuryloxycarbonyl,
Z: benzyloxycarbonyl,
Z(p-Cl): 4-chlorobenzyloxycarbonyl, or
Z(p-OMe): 4-methoxybenzyloxycarbonyl; and (β) groups of the benzyl type, for example:
Bn: phenylmethyl.

Among these amino-protecting groups, the preferred groups are the groups Boc and Bn.

In practical terms, the method of preparing a compound of formula I or one of its addition salts comprises the steps which consist in:

(i) deprotecting a compound of formula II:

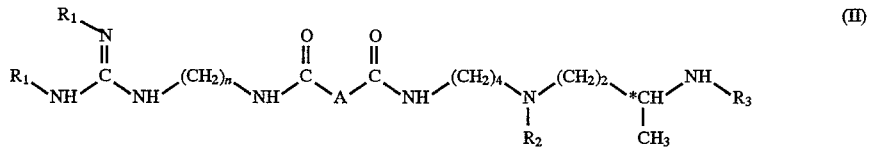
(II)

in which:
A is a single bond, a group $CH_2$, a group CHF, a group $CH(OCH_3)$, a group $CH(OH)$, a group $CH(OCH_2C_6H_5)$, a group $CH_2O$ or a group $CH_2NH$,
n is equal to 6 or 8, and
$R_1$, $R_2$ and $R_3$, which are identical or different, are each an amino-protecting group of the alkoxycarbonyl, benzyloxycarbonyl or benzyl type, by one or more treatments, depending on the nature of the amino-protecting groups, for example if at least one of the radicals $R_1$, $R_2$ or $R_3$ is a group of the oxycarbonyl type, by reaction with a strong acid such as trifluoroacetic acid in particular, or if at least one of the radicals $R_1$, $R_2$ or $R_3$ is a group of the benzyl type or if A is the group $CH(OCH_2C_6H_5)$, by catalytic hydrogenation in the presence of palladium-on-charcoal or a palladium salt, to give a compound of formula I in the form of the free base or one of its addition salts; and (ii) if necessary, starting from an addition salt prepared according to step (i), obtaining the compound of formula I in the form of the free base by reaction with a strong base, and then obtaining the other addition salts from said free base.

A compound of formula II can be prepared by using a variant selected from the following:

(a) variant A, which comprises the step consisting in: condensing a compound of the formula

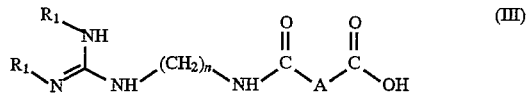
(III)

in which:
n is equal to 6 or 8,
A is the group $CH_2$, $CH(OCH_3)$, $CH(OCH_2C_6H_5)$ or CHF or a single bond, and
$R_1$ is an amino-protecting group, for example the group Boc,
with an amine of the formula

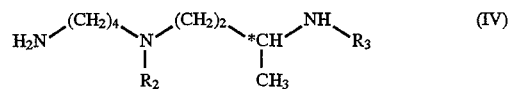
(IV)

in which:
$R_2$ and $R_3$, which are identical or different, are each an amino-protecting group, for example the groups Boc or benzyl (Bn),
by activation of the acid:
either with a coupling agent of the carbodiimide type (especially 1,3-dicyclohexylcarbodiimide), in the presence of a nucleophilic agent (for example 1-hydroxybenzotriazole), in an organic solvent, especially a chlorinated solvent, for example chloroform or dichloromethane, and at a temperature of between 0° C. and 40° C., or by the formation of a mixed anhydride, for example with isobutyl chloroformate, in the presence of a basic agent such as N-methylmorpholine in particular, in an organic solvent, especially tetrahydrofuran, and at a temperature of between −35° C. and +20° C., at a rate of 1 mol of the compound III to about 1 mol of the compound IV, to give a compound of the formula

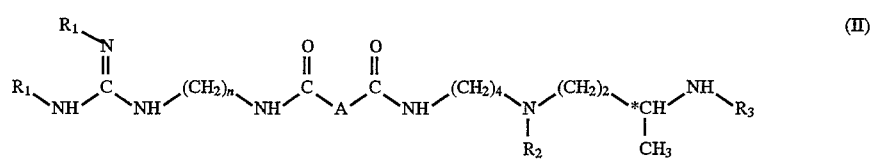
(II)

in which n, A, $R_1$, $R_2$ and $R_3$ are defined as indicated above;

(b) variant B, which comprises the steps consisting in:
(i) reacting a compound of the formula

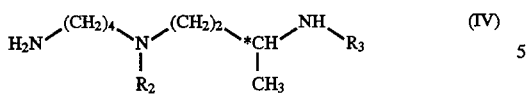 (IV)

in which:

$R_2$ and $R_3$, which are identical or different, are each an amino-protecting group of the oxycarbonyl or benzyl type, with an acid or an acid chloride of the formula

 (V)

in which:

X is a chlorine atom or a group OH,

A is a single bond, a group $CH_2$, a group CHF, a to group $CH(OCH_3)$ or a group $CH(OCH_2C_6H_5)$, and $R_4$ is a linear or branched $C_1$–$C_3$-alkyl group or a phenylmethyl group, in an organic solvent, especially a chlorinated solvent, for example dichloromethane or chloroform, in the presence of a carboxyl group activator, for example a carbodiimide (especially 1,3-dicyclohexylcarbodiimide or carbonyldiimidazole), and a nucleophilic agent (especially 1-hydroxybenzotriazole) if X is the group OH, or in the presence of a tertiary amine (for example triethylamine) if X is a chlorine atom, at a temperature of between 0° C. and 40° C., at a rate of 1 mol of IV to about 1 mol of V, to give a compound of the formula

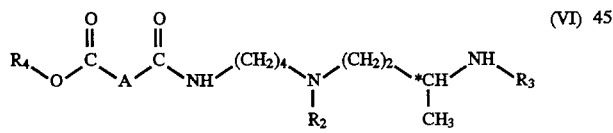 (VI)

in which A, $R_2$, $R_3$ and $R_4$ are defined as indicated above;

(ii) saponifying the resulting compound of formula VI in an organic solvent, in the presence of a strong base, to give a compound of the formula

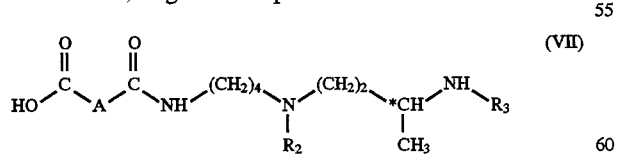 (VII)

in which A, $R_2$ and $R_3$ are defined as indicated above; and (iii) condensing the resulting compound of formula VII with an amine of the formula

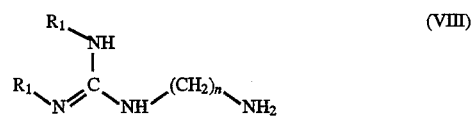 (VIII)

in which:

n is equal to 6 or 8, and $R_1$ is an amino-protecting group, for example a group Boc, under conditions identical to those of variant A above, to give a compound of the formula

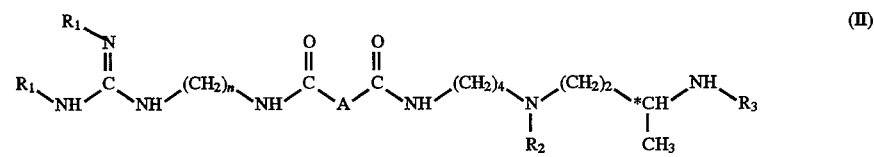 (II)

in which A, n, $R_1$, $R_2$ and $R_3$ are defined as indicated above;

(c) variant C, which comprises the steps consisting in:
(i) acylating the terminal $NH_2$ end of a base of the formula

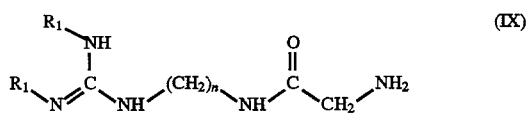 (IX)

in which $R_1$ is an amino-protecting group, especially the group Boc, and n is equal to 6 or 8, with a chloroformate or a symmetrical carbonate [especially bis(4-nitrophenyl) carbonate] in an inert solvent (for example dichloromethane), at room temperature (15°–25° C.); and (ii) aminolyzing the resulting compound with an amine of the formula

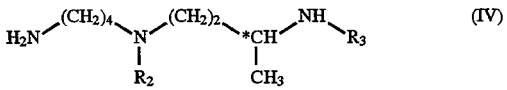 (IV)

in which:

$R_2$ and $R_3$, which are identical or different, are each an amino-protecting group, especially a group Boc or a phenylmethyl group, in an inert solvent such as dichloromethane in particular, to give a compound of the formula

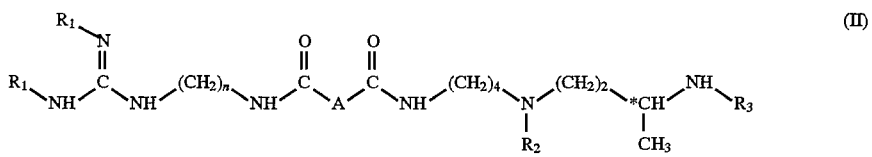
(II)

in which n, $R_1$, $R_2$ and $R_3$ are as defined above and A is the group —$CH_2$—NH—; and (d) variant D, which comprises the steps consisting in:
(i) reacting an amine of the formula

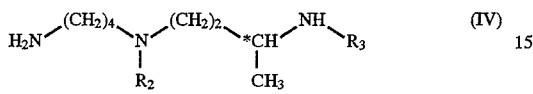
(IV)

in which:
$R_2$ and R3, which are identical or different, are each an amino-protecting group,
with a carbonate of the formula

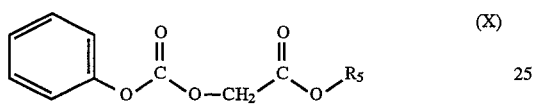
(X)

in which $R_5$ is a $C_1$-$C_3$-alkyl group or a phenylmethyl group, in an inert solvent (especially an aromatic solvent, for example toluene), at a temperature between room temperature and the reflux temperature of the reaction medium, at a rate of 1 mol of IV to about 1 mol of X, to give a compound of the formula

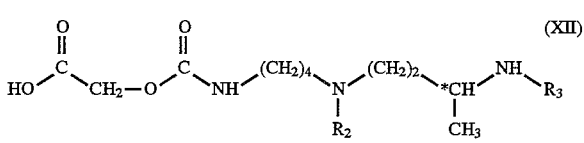
(XII)

in which $R_2$ and $R_3$ are as defined above; and (iii) condensing the resulting compound of formula XII with an amine of the formula

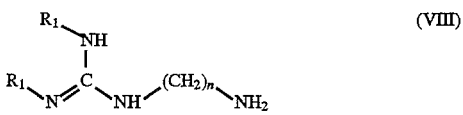
(VIII)

in which n is equal to 6 or 8 and $R_1$ is an amino-protecting group, especially the group Boc, under conditions identical to those described for variant A above, to give a compound of the formula

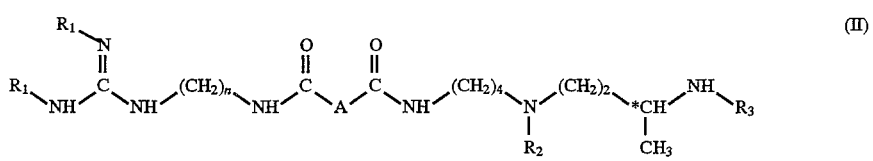
(II)

in which n, $R_1$, $R_2$ and $R_3$ are as defined above and A is a group $CH_2O$.

The invention will be understood more clearly from the description of the Examples which follow and, the results of pharmacological tests obtained with the compounds according to the invention, compared with the results obtained with known products of the prior art. The nomenclature used for the Examples is that proposed by Chemical Abstracts; according to this nomenclature, a monoester of an alkanedioic acid with t-butanol is referred to here as "1,1-dimethylethyl alkanedioate" and a diester of the type t-butyl ethyl alkanedioate is referred to here as "1,1-dimethylethyl ethyl alkanedioate".

In the experimental section, the Preparations relate to the intermediates and the Examples relate to the products according to the invention.

If the compounds contain an asymmetric carbon in their structure, the absence of any particular indication means that they are a substantially equimolecular mixture of the two enantiomers (racemate).

If these same compounds are referred with the symbol (R) or (S) immediately following the identification of the position of a substituent, this means that the carbon carrying this substituent has the (R) or (S) configuration as defined by the Cahn-Ingold-Prelog rules.

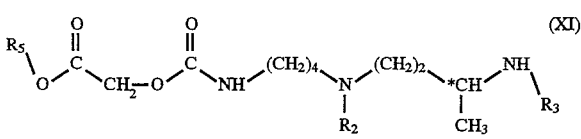
(XI)

in which $R_2$, $R_3$ and $R_5$ are as defined above, or a compound of the formula

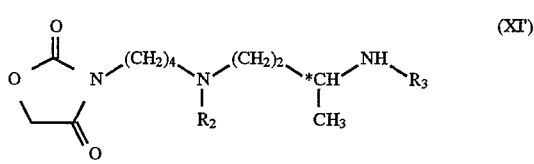
(XI')

in which $R_2$ and $R_3$ are as defined above;

(ii) saponifying the resulting compound XI or XI' in an organic solvent, in the presence of a strong base, to give a compound of the formula If the compounds contain two centers of asymmetry in their structure, the absence of any particular indication means that they are a mixture of the four diastereoisomers.

The spectral characteristics of the nuclear magnetic resonance (NMR) signals are given for the proton ($^1$H) or for the 13 isotope of carbon ($^{13}$C). The following are indicated: the chemical shift relative to the signal for TMS, the shape of the signal (s for singlet, d for doublet, t for triplet, q for quadruplet, m for multiplet, bs for broad signal) and the number of protons to which the signal applies. By way of indication, the $^1$H NMR spectra were run at 300 MHz.

PREPARATION 1

4-[N-(3-Hydroxybutyl)-N-(phenylmethyl)amino]butanenitrile 5 g (28.10$^{-3}$ mol) of 3-[N-(phenylmethyl)amino]-1-methylpropanol are dissolved in 60 ml of butanol, and 3.56 g (34.10$^{-3}$ mol) of sodium carbonate, 1.06 g (7.10$^{-3}$ mol) of potassium iodide and then a solution of 7.4 g (70.10$^{-3}$ mol) of 4-chlorobutyronitrile in 10 ml of butanol are added. The reaction mixture is refluxed for 20 hours, with stirring. After cooling, it is filtered and the insoluble materials are rinsed with 60 ml of ethyl ether. The combined filtrates are concentrated under reduced pressure and the resulting residue is taken up with 100 ml of dichloromethane.

The solution obtained is extracted with 50 ml of 1M hydrochloric acid; the acid aqueous phase obtained is washed twice with 50 ml of dichloromethane and then rendered basic by the slow addition of 50 ml of a 5N solution of sodium hydroxide. The product is extracted from the aqueous phase with 3 times 50 ml of dichloromethane. The organic phase obtained is dried over potassium carbonate and then concentrated under reduced pressure. The yellow liquid obtained (7 g) is then distilled under vacuum to give 6.02 g (yield=87%) of the expected product.

B.p.=160°–170° C./0.05 mm Hg. (0.05 mm Hg corresponds to about 0.066 Pa.)

PREPARATION 2

3-[N-(3-Cyanopropyl)-N-(phenylmethyl)amino]-1-methylpropyl methanesulfonate

A solution of 9.11 g (37.10$^{-3}$ mol) of the product obtained according to Preparation 1 is prepared in 150 ml of anhydrous ethyl ether and cooled to 0° C. 11.23 g (111.10$^{-3}$ mol) of triethylamine are then added, after which 4.66 g (40.10$^{-3}$ mol) of methanesulfonyl chloride are added dropwise. The mixture is stirred at 0° C. for 1 hour after the addition has ended, and then for 15 hours at room temperature. 120 ml of a saturated solution of sodium bicarbonate are added slowly and the reaction medium is then extracted with 3 times 50 ml of ethyl ether. The organic phases are combined, dried over potassium carbonate and then concentrated under reduced pressure to give 11.7 g (yield=98% of crude product) of the expected product in the form of a viscous yellow oil. The product is used without further purification in the next step but can be obtained pure by chromatography on silica using an n-heptane/ethyl ether mixture (7/3 v/v) as the eluent. $^1$H NMR (CDCl$_3$): 1.33 (d, 3H); 1.76 (m, 3H); 1.86 (m, 1H); 2.37 (t, 2H); 2.53 (m, 4H); 2.89 (s, 3H); 3.48 (d, 1H); 3.57 (d, 1H); 4.84 (m, 1H); 7.28 (m, 5H).

PREPARATION 3

3-[N-(3-Cyanopropyl)-N-(phenylmethyl)amino]-1-methyl-1-azidopropane

A solution of 10.59 g (33.10$^{-3}$ mol) of the product of Preparation 2 is prepared in 70 ml of dimethyl sulfoxide, and 6.43 g (100.10$^{-3}$ mol) of sodium nitride are added. The reaction mixture is stirred for 15 hours at 45°–50° C. and then cooled; 100 ml of water are added and the mixture is then extracted with 100 ml of ethyl ether. The decanted aqueous phase is re-extracted 3 times with 30 ml of ethyl ether and the combined organic phases are washed with 50 ml of a saturated aqueous solution of sodium chloride and then dried over magnesium sulfate. After removal of the solvent under reduced pressure, the residual liquid is purified by chromatography on silica using an n-heptane/ethyl ether mixture (7/3 v/v) as the eluent to give 7.8 g (yield=78%) of the expected product in the form of a viscous colorless oil. $^1$H NMR (CDCl$_3$): 1.22 (d, 3H); 1.58 (m, 2H); 1.77 (m, 2H); 2.34 (t, 2H); 2.52 (m, 4H); 3.50 (m, 3H); 7.26 (m, 5H).

PREPARATION 4

1,1-Dimethylethyl 9-cyano-3-methyl-6-(phenylmethyl)-2,6-diazanonanoate 3.00 g (11.10$^{-3}$ mol) of the product obtained according to Preparation 3 and 2.85 g (13.10$^{-3}$ mol) of ditert-butyl dicarbonate (product of the structure O[COC(CH$_3$)$_3$]$_2$) in solution in 30 ml of anhydrous ethyl acetate are introduced into a 250 ml hydrogenation flask and 0.3 g of 10% palladium-on-charcoal is added. The mixture is hydrogenated for 15 hours at room tem- perature under a pressure of 2.10$^5$ Pa, with stirring. The catalyst is subsequently filtered off and the filtrate is then concentrated under reduced pressure.

The residual product is purified by chromatography on silica gel using an n-heptane/ethyl ether mixture (45/55 v/v) as the eluent to give 3.47 g (yield=91%) of the expected product in the form of a viscous colorless oil.

$^1$H NMR (CDCl$_3$): 1.06 (d, 3H); 1.44 (s, 9H); 1.45–1.80 (m, 4H); 2.33 (t, 1H); 2.48 (m, 3H); 3.50 (q, 2H); 3.70 (bs, 1H); 5.08 (bs, 1H); 7.27 (m, 5H).

PREPARATION 5

1,1-Dimethylethyl 10-amino-3-methyl-6-(phenylmethyl)-2,6-diazadecanoate

A suspension of 2 g of Raney nickel in 180 ml of anhydrous ethanol is introduced into a hydrogenation apparatus. This suspension is saturated by the bubbling of gaseous ammonia for 10 minutes, and a solution of 2.95 g (8.10$^{-3}$ mol) of the product obtained in Preparation 4 in 20 ml of anhydrous ethanol is then added. The reaction mixture is then hydrogenated for 15 hours at 40° C. under a pressure of 10$^6$ Pa.

After cooling, the catalyst is filtered off and the filtrate is concentrated under reduced pressure. The residual oil is purified by chromatography on silica gel using a methanol/32% aqueous ammonia mixture (100/1 v/v) as the eluent to give 2.7 g (yield=91%) of the expected product in the form of a viscous colorless oil.

$^1$H NMR (CDCl$_3$): 1.04 (d, 3H); 1.31 (s, 2H); 1.44 (s, 9H); 1.30–1.75 (m, 6H); 2.63 (t, 2H); 2.25–2.70 (m, 4H); 3.43 (d, 1H); 3.60 (d, 1H); 3.60–3.75 (m, 1H); 5.74 (bs, 1H); 7.30 (m, 5H).

PREPARATION 6

1-(1,1-Dimethylethyl) 14-ethyl 3-[[(1,1-dimethylethoxy)carbonyl]amino]-12-oxo-2,4,11-triazatetradec-2-enedioate 1.05 g (8.10$^{-3}$ mol) of monoethyl malonate are dissolved in 15 ml of anhydrous chloroform, the solution is then cooled to 0° C. and 1.65 g (8.10$^{-3}$ mol) of 1,3-dicyclohexylcarbodiimide and 0.108 g (0.8.10$^{-3}$ mol) of 1-hydroxybenzotriazole hydrate are added. After stirring for 0.5 hour at 0° C., a solution of 1.5 g (4.19.10$^{-3}$ mol) of bis(1,1-dimethylethyl) [[(6-aminohexyl)imino]methylene]biscarbamate in 5 ml of anhydrous chloroform is added. The mixture is then stirred for 48 hours at room temperature, after which the reaction medium is concentrated under reduced pressure. The crude product obtained is purified by medium pressure chromatography on silica using a hexane/ ethyl acetate mixture (1/1 v/v) as the eluent to give 1.95 g (yield=99%) of the expected product in the form of a yellow oil.

$^1$H NMR (CDCl$_3$): 1.30 (t, 3H); 1.35–1.65 (m, 26H); 3.2–3.35 (m, 4H); 3.4 (td, 2H); 4.2 (q, 2H); 7.1–7.2 (bs, 1H); 8.3 (t, 1H); 11.5 (s, 1H).

PREPARATION 7

1-(1,1-Dimethylethyl) 3-[[(1,1-dimethylethoxy)carbonyl] amino]-12-oxo-2,4,11-triazatetradec-2-enedioate 1.95 g (4.15.10$^{-3}$ mol) of the product obtained in Preparation 6 above are dissolved in 15 ml of dimethoxyethane, and 8.5 ml of a 1 N aqueous solution of NaOH are added. The mixture is stirred at room temperature for 15 min, 25 ml of water and 25 ml of chloroform are then added and the mixture is acidified slowly to pH 2 with a 1N aqueous solution of HCl. It is extracted several times with chloroform and the organic phase is then dried and concentrated under reduced pressure to give 1.8 g (yield=100%) of the expected product in the form of a thick yellow-colored oil.

$^1$H NMR (CDCl$_3$): 1.35–1.65 (m, 26H); 3.3–3.45 (m, 6H); 7.05 (bs, 1H); 8.3 (t, 1H); 9–11.5 (bs, 2H).

PREPARATION 8

Bis(1,1-dimethylethyl) 3-[[(1,1-dimethylethoxy)carbonyl] amino]-23-methyl-12,14-dioxo-20-(phenylmethyl)-2,4,11,15,20,24-hexaazapentacos-2-enedioate By following a procedure analogous to Preparation 6, except that 6.21 g (14.10$^{-3}$ mol) of the product obtained in Preparation 7 and 4.7 g (13.5.10$^{-3}$ mol) of 1,1-dimethylethyl 10-amino-3-methyl-6-(phenylmethyl)-2,6-diazadecanoate are used as the starting materials, 8.5 g (yield=81%) of the expected product are obtained in the form of an orange oil after purification by chromatography on silica using an ethyl acetate/ethanol mixture (9/1 v/v) as the eluent.

$^1$H NMR (CDCl$_3$): 1.01–1.03 (d, 3H); 1.23–1.70 (m, 41H); 2.4–2.7 (m, 4H); 3.05–3.3 (m, 6H); 3.35–3.45 (td, 2H); 3.6–3.8 (m, 3H); 5.1–5.4 (bs, 1H); 7.1–7.4 (m, 5H); 7.55 (bs, 1H); 7.75 (bs, 1H); 8.3 (t, 1H); 11.5 (s, 1H).

PREPARATION 9

Bis(1,1-dimethylethyl) 3-[[(1,1-dimethylethoxy)carbonyl] amino]-23-methyl-12,14-dioxo-2,4,11,15,20,24-hexaazapentacos-2-enedioate hydrochloride 8.5 g (10.9.10$^{-3}$ mol) of the product obtained according to Preparation 8 are dissolved in 100 ml of ethanol, and 0.57 g of palladium chloride and 0.7 ml of concentrated hydrochloric acid are added. The mixture is then hydrogenated at atmospheric pressure for 8 hours. The catalyst is filtered off and rinsed with a small amount of ethanol and the resulting filtrate is then concentrated under reduced pressure to give 7.8 gl (yield=98%) of the expected product in the form of a colorless oil.

$^1$H NMR (CDCl$_3$): 1.20 (d, 3H); 1.25–1.9 (m, 41H); 2.55–2.80 (m, 2H); 2.80–3.55 (m, 10H); 3.75 (bs, 1H); 4.9 (d, 1H); 7.9 (m, 1H); 8.23 (bs, 1H); 8.3 (t, 1H); 11.5 (s, 1H).

EXAMPLE 1

N-[4-[[3-(Amino)butyl]amino]butyl]-N'-[6-[(aminoiminomethyl)amino]hexyl]propanediamide tris (trifluoroacetate)

7.8 g (10.8.10$^{-3}$ mol) of the product obtained according to Preparation 9 above are dissolved in 40 ml of dichloromethane, and 40 ml of trifluoroacetic acid are added. The reaction mixture is stirred for 5 hours at room temperature and then concentrated under reduced pressure. The residual oil is purified by medium pressure chromatography on RP18 grafted silica (particle size: 5–20 micrometers) using a water/acetonitrile/trifluoroacetic acid mixture (8/1/1 v/v) as the eluent. The pure fractions thus obtained are combined and lyophilized. The lyophilizate is then taken up with 100 ml of water, the solution is washed with twice 100 ml of ethyl acetate and the aqueous phase is then lyophilized again. This operation is repeated twice to remove the trifluoroacetic acid. This gives 4.5 g (yield= 57%) of the expected product in the form of an amorphous solid.

$^1$H NMR (DMSO-d$_6$): 1.15–1.20 (d, 3H); 1.25–1.5 (m, 8H); 1.5–1.85 (m, 4H); 1.85–2.0 (m, 2H); 2.85–3.2 (m, 12H); 3.25–3.35 (m, 1H); 6.8–7.55 (bs, 3H); 7.6 (t, 1H); 7.9–8.1 (m, 5H); 8.5–8.75 (bs, 3H).

$^{13}$C NMR (D$_2$O): 18.01; 23.71; 26.21; 26.24; 26.35; 28.56; 28.84; 31.22; 39.51; 40.31; 41.88; 44.30; 44.60; 46.10; 48.14; 157.55; 170.01; 170.34.

PREPARATION 10

1,1-Dimethylethyl 3-methyl-10-[2,4-dioxooxazolidin-3-yl]-6-(phenylmethyl)-2,6-diazadecanoate A solution of 3 g (8.6.10$^{-3}$ mol) of 1,1-di-methylethyl 10-amino-3-methyl-6-phenylmethyl-2,6-diazadecanoate is prepared in 50 ml of anhydrous toluene and a solution of 1.8 g (8.6.10$^{-9}$ mol) of methyl phenoxycarbonyloxyacetate in 10 ml of anhydrous toluene is added, followed by 1.08 g (10.7.10$^{-3}$ mol) of triethylamine. The mixture is heated to 60° C. and kept at this temperature for 48 hours, with stirring. The reaction medium is then concentrated under reduced pressure and, the resulting residue is purified by chromatography on silica using a methylcyclohexane/ethyl acetate mixture (1/1 v/v) as the eluent to give 3.1 g (yield= 82%) of product in the form of a viscous yellow oil.

$^1$H NMR (CDCl$_3$): 1.0–1.1 (d, 3H); 1.4–1.7 (m, 15H); 2.35–2.50 (m, 3H); 2.50–2.65 (m, 1H); 3.40–3.60 (m, 4H); 3.60–3.75 (m, 1H); 4.65 (s, 2H); 5.35 (bs, 1H); 7.2–7.3 (m, 5H).

PREPARATION 11

1-(1,1-Dimethylethyl) 3-methyl-6-(phenylmethyl)-13-oxa-12-oxo-2,6,11-triazapentadecanedioate 3.1 g (7.1.10$^{-3}$ mol) of the product obtained according to Preparation 10 above are dissolved in 20 ml of dimethoxyethane, and 21 ml of a 1N aqueous solution of NaOH are then added. The mixture is stirred at room temperature for 4 hours and 75 ml of water and 75 ml of dichloromethane are then added. The mixture is acidified to pH 2 with a 1N solution of hydrochloric acid and extracted with dichloromethane. The organic phases are washed once with a solution of sodium chloride, dried over magnesium sulfate and then concentrated under reduced pressure to give 3 g (yield=93%) of the expected product in the form of a thick yellow oil.

$^1$H NMR (CDCl$_3$): 1.15 (d, 3H); 1.2–2.2 (m, 15H); 2.35–2.55 (t, 2H); 2.7–2.9 (t, 2H); 2.9–3.3 (m, 4H); 3.5–3.75 (m, 1H); 4.0–4.3 (m, 2H); 4.9 (d, 1H); 5.1 (d, 1H); 7.4–7.8 (m, 5H); 12.3 (bs, 1H).

PREPARATION 12

Bis(1,1-dimethylethyl) 3-[[(1,1-dimethylethoxy)carbonyl] amino]-24-methyl-21-(phenylmethyl)-14-oxa-12,15- dioxo-2,4,11,16,21,25-hexaazahexacos-2-enedioate By following a procedure analogous to Preparation 6, except that dichloromethane is used as the solvent and 3 g (6.65.10$^{-3}$ mol) of the acid obtained according to Preparation 11 and 2.61 g (6.65.10$^{-3}$ mol) of bis(1,1-dimethylethyl) [[(6-aminohexyl)imino]methylene]biscarbamate are used as the starting materials, 4 g (yield=76%) of the expected product are obtained in the form of a yellow oil after purification by chromatography on silica using a methylcyclohexane/ethyl acetate mixture (3/7 v/v) as the eluent.

$^1$H NMR (CDCl$_3$): 0.9–1.1 (d, 3H); 1.25–1.75 (m, 41H); 2.3–2.5 (m, 3H); 2.6 (m, 1H); 3.1–3.2 (bs, 2H); 3.2–3.35 (q,

2H); 3.35–3.45 (t, 2H); 3.5 (q, 2H); 3.7 (m, 1H); 4.5 (s, 2H); 5.3–5.6 (bs, 2H); 6.3 (bs, 1H); 7.2–7.3 (m, 5H); 8.3 (t, 1H); 11.5 (s, 1H).

PREPARATION 13

2-[[[4-[N'-[3-(Amino)butyl]-N'-[phenylmethyl]amino]butyl]amino]carbonyloxy]-N-[6-[(aminoiminomethyl)amino]hexyl]acetamide tris(trifluoroacetate)

By following a procedure analogous to Example 1, except that 4 g of the product obtained according to Preparation 12 above are used as the starting material, 4.2 g (yield=99%) of the expected product are obtained in the form of a thick oil after purification by chromatography on a column of RP18 grafted silica using a water/acetonitrile/trifluoroacetic acid mixture (7.5/2/0.5 v/v) as the eluent.

$^1$H NMR (CDCl$_3$): 1.1–1.2 (d, 3H); 1.2–1.6 (m, 10H); 1.65–2.2 (m, 4H); 2.9–3.2 (m, 12H); 3.2–3.35 (m, 1H); 4.35 (s, 2H); 6.8–7.3 (bs, 1H); 7.35 (t, 1H); 7.45–7.65 (m, 5H); 7.85–8.1 (m, 3H); 9.8 (s, 1H).

EXAMPLE 2

2-[[[4-[[3-(Amino)butyl]amino]butyl]amino]carbonyloxy]-N-[6-[(aminoiminomethyl)amino]hexyl]acetamide tris(trifluoroacetate)

4.2 g (5.05.10$^{-3}$ mol) of the product obtained in Preparation 13 above are dissolved in 275 ml of methanol, and 0.25 ml of concentrated hydrochloric acid is then added, followed by 0.25 g of palladium chloride. The mixture is then hydrogenated at atmospheric pressure and at room temperature for 14 hours. The reaction medium is filtered and then concentrated under reduced pressure. The oil obtained is taken up with 100 ml of water and 1 ml of trifluoroacetic acid and the solution is then washed with 3 times 75 ml of ethyl acetate and lyophilized to give 3.9 g (yield=99%) of the expected product in the form of an amorphous solid.

$^1$H NMR (DMSO-d$_6$): 1.2 (d, 3H); 1.25–1.70 (m, 12H); 1.70–1.9 (m, 1H); 1.9–2.05 (m, 1H); 2.85–3.15 (m, 11H); 4.3 (s, 2H); 6.8–7.5 (m, 5H); 7.6–7.75 (t, 1H); 7.85–7.95 (t, 1H); 7.95–8.20 (bs, 3H); 8.70–8.90 (bs, 2H).

$^{13}$C NMR (D$_2$O): 18.02; 23.65; 26.19; 26.28; 26.76; 28.56; 28.93; 31.22; 39.77; 40.59; 41.88; 44.61; 46.11; 48.22; 63.76; 157.54; 158.21; 171.45.

PREPARATION 14

Bis(1,1-dimethylethyl) 3-[[(1,1-dimethylethoxy)carbonyl]amino]-25-methyl-22-phenylmethyl-14,16-dioxo-2,4,13,17,22,26-hexaazaheptacos-2-enedioate By following a procedure identical to Preparation 6, except that 2.1 g (4.45.10$^{-3}$ mol) of 1-(1,1-dimethylethyl) 3-[[(1,1-dimethylethoxy)carbonyl]amino]-14-oxo-2,4,13-triazahexadec-2-enedioate and 1.55 g (4.45.10$^{-3}$ mol) of the compound obtained in Preparation 5 are used as the starting materials, 3.26 g (yield=93%) of the expected product are obtained in the form of an amorphous yellow solid after purification by chromatography on silica gel using an ethyl acetate/ethanol/aqueous ammonia mixture (7/3/0.1 v/v) as the eluent.

$^1$H NMR (CDCl$_3$): 1.02 (d, 3H); 1.2–1.8 (m, 45H); 2.55–2.8 (m, 4H); 3.1–3.3 (m, 6H); 3.38 (td, 2H); 3.5–3.7 (m, 1H); 3.7–3.9 (m, 2H); 5–5.3 (bs, 1H); 7.1–7.45 (m, 5H); 7.5–7.6 (bs, 1H); 7.7–7.8 (bs, 1H); 8.3 (t, 1H); 11.5 (s, 1H).

PREPARATION 15

Bis(1,1-dimethylethyl) 3-[[(1,1-dimethylethoxy)carbonyl]amino]-25-methyl-14,16-dioxo-2,4,13,17,22,26-hexaazaheptacos-2-enedioate 3.2 g (4.06.10$^{-3}$ mol) of the compound obtained according to Preparation 14 are dissolved in 75 ml of ethanol, and 0.25 g of 5% palladium-on-charcoal is added. The mixture is hydrogenated at room temperature and at atmospheric pressure for 12 hours. The catalyst is filtered off and the filtrate is concentrated under reduced pressure to give 2.15 g (yield=74%) of the expected product in the form of an amorphous solid.

$^1$H NMR (CDCl$_3$): 1.15 (d, 3H); 1.25–1.8 (m, 45H); 2.55–2.7 (m, 4H); 3.11 (s, 2H); 3.2–3.3 (m, 4H); 3.39 (td, 4H); 3.65–3.8 (m, 1H); 4.8–4.9 (m, 1H); 7.05 (bs, 1H); 7.55 (bs, 1H); 8.3 (t, 1H); 11.5 (s, 1H).

EXAMPLE 3

N-[4-[[3-(Amino)butyl]amino]butyl]-N'-[8-[(aminoiminomethyl)amino]octyl]propanediamide tris(trifluoroacetate)

By following a procedure analogous to Example 1, except that 2.15 g (3.01.10$^{-3}$ mol) of the compound obtained according to Preparation 15 are used as the starting material, 2.05 g (yield=90%) of the expected product are obtained in the form of an amorphous solid after purification on RP18 silica gel using a water/acetonitrile/trifluoroacetic acid mixture (7.5/2/0.5 v/v) as the eluent.

$^1$H NMR (DMSO-d$_6$): 1.18 (d, 3H); 1.2–1.65 (m, 16H); 1.65–1.8 (m, 1H); 1.8–2 (m, 1H); 2.8–3.1 (m, 12H); 3.25–3.3 (m, 1H); 6.8–7.5 (bs, 3H); 7.55 (t, 1H); 7.85–8.1 (m, 5H); 8.45–8.65 (m, 3H).

$^{13}$C NMR (D$_2$O): 18.01; 23.69; 26.24; 26.51; 26.69; 28.60; 28.92; 28.96; 32.21; 39.49; 40.46; 41.97; 44.31; 44.59; 46.10; 48.14; 157.89; 169.96; 170.34.

PREPARATION 16

Bis(1,1-dimethylethyl) 3-[[(1,1-dimethylethoxy)carbonyl]amino]-23-methyl-20-(phenylmethyl)-13-(phenylmethoxy)-12,14-dioxo-2,4,11,15,20,24-hexaazapentacos-2-enedioate 2.78 g (5.05.10$^{-3}$ mol) of 1-(1,1-dimethylethyl) 3-[[(1,1-dimethylethoxy)carbonyl]amino]-13-(phenylmethoxy)-12-oxo-2,4,11-triazatetradec-2-enedioate are dissolved in 50 ml of anhydrous tetrahydrofuran (THF). The solution is cooled to −25° C. and 1.02 g (10.1.10$^{-3}$ mol) of N-methylmorpholine and 0.69 g (5.05.10$^{-3}$ mol of isobutyl chloroformate are added. A white precipitate forms immediately. The mixture is stirred for 0.5 hour and a solution of 1.76 g (5.05.10$^{-3}$ mol) of the compound obtained according to Preparation 5 in 10 ml of THF is then added. The mixture is stirred for 1 hour and then concentrated under reduced pressure. The product is purified by chromatography on silica gel using a methylcyclohexane/ethyl acetate mixture (7.5/2.5 v/v) as the eluent to give 3.76 g (yield=86%) of the expected product in the form of a yellow oil.

$^1$H NMR (CDCl$_3$): 1.04 (dd, 3H); 1.2–1.8 (m, 41H); 2.3–2.7 (m, 4H); 3.1–3.3 (m, 4H); 3.3–3.5 (m, 3H); 3.5–3.75 (m, 2H); 4.28 (s, 1H); 4.79 (s, 2H); 5.3–5.5 (bs, 1H); 6.95 (bs, 1H); 7.2–7.4 (m, 10H); 8.3 (t, 1H); 11.5 (s, 1H).

PREPARATION 17

Bis(1,1-dimethylethyl) 3-[[(1,1-dimethylethoxy)carbonyl]amino]-13-hydroxy-23-methyl-12,14-dioxo-2,4,11,15,20,24-hexaazapentacos-2-enedioate By following a procedure analogous to Preparation 15, except that 3.76 g (4.35.10$^{-3}$ mol) of the product obtained according to Preparation 16 are used as the starting material, 3.05 g (quantitative yield) of the expected product are obtained in the form of a yellow oil.

$^1$H NMR (CDCl$_3$): 1.15 (d, 3H); 1.25–1.75 (m, 42H); 2.55–2.7 (m, 4H); 3.1–3.35 (m, 4H); 3.35–3.45 (td, 2H); 3.6–3.8 (m, 1H); 4.42 (s, 1H); 4.75–4.85 (m, 1H); 7.2–7.45 (m, 3H); 8.3 (t, 1H); 11.5 (s, 1H).

EXAMPLE 4

N-[4-[[3-(Amino)butyl]amino]butyl]-N'-[6-[(aminoiminomethyl)amino]hexyl]-2-hydroxypropanediamide tris(trifluoroacetate)

By following a procedure analogous to Example 1, using 3.03 g (4.32.10$^{-3}$ mol) of the compound obtained according to Preparation 17 as the starting material, 1.89 g (yield= 60%) of an amorphous white solid are obtained after purification by chromatography on RP18 silica gel using a water/acetonitrile/trifluoroacetic acid mixture (8/1/1 v/v) as the eluent.

$^{1}$H NMR (DMSO-d$_6$): 1.18 (d, 3H); 1.2–1.65 (m, 12H); 1.65–1.85 (m, 1H); 1.85–2 (m, 1H); 2.8–3.15 (m, 10H); 3.2–3.35 (m, 1H); 4.31 (s, 1H); 6.7–7.4 (m, 3H); 7.6 (t, 1H); 7.85–8.05 (m, 5H); 8.45–8.65 (m, 3H).

$^{13}$C NMR (D$_2$O): 18.01; 23.66; 26.19; 26.28; 26.31; 28.55; 28.94; 31.21; 39.22; 40.00; 41.87; 44.59; 46.09; 48.12; 73.13; 157.23; 171.20; 171.53.

PREPARATION 18
1-(1,1-Dimethylethyl) 16-ethyl 3-[[(1,1-dimethylethoxy)carbonyl]amino]-15-phenylmethoxy-14-oxo-2,4,13-triazahexadec-2-enedioate 2.6 g (10.9.10$^{-3}$ mol) of ethyl 2-phenylmethoxypropanedioate are dissolved in 50 ml of dichloromethane and the mixture is cooled to 0° C. 4.34 g (22.10$^{-3}$ mol) of N,N'-dicyclohexylcarbodiimide and 0.57 g (4.10$^{-3}$ mol) of 1-hydroxybenzotriazole are added, the mixture is stirred for 0.5 hour, a solution of 4.21 g (10.9. 10$^{-3}$ mol) of bis(1,1-dimethylethyl) [[(8-aminooctyl)imino]methylene]biscarbamate in 15 ml of dichloromethane is then added and the mixture is stirred at room temperature for 48 hours. The reaction medium is concentrated under reduced pressure and the residue is then purified by chromatography on silica using a methylcyclohexane/ethyl acetate mixture (7/3) as the eluent to give 2.7 g (yield=40.8%) of the expected product in the form of a pale yellow oil.

$^{1}$H NMR (CCDl$_3$): 1.25–1.6 (m, 33H); 3.25 (td, 2H); 3.39 (td, 2H); 4.25 (q, 2H); 4.44 (s, 1H); 4.54 (d, 1H); 4.70 (d, 1H); 6.62 (t, 1H); 7.3–7.45 (m, 5H); 8.28 (t, 1H); 11.5 (s,1H).

PREPARATION 19
1-(1,1-Dimethylethyl) 3-[[(1,1-dimethylethoxy)carbonyl]amino]-15-phenylmethoxy-14-oxo-2,4,13-triazahexadec-2-enedioate By following a procedure analogous to Preparation 7, using 2.7 g (4.45.10$^{-3}$ mol) of the compound obtained according to Preparation 18 as the starting material, 2.55 g (yield=99%) of the expected product are obtained in the form of a yellow oil.

$^{1}$H NMR (CDCl$_3$): 1.2–1.7 (m, 30H); 3.2–3.4 (m, 4H); 4.41 (s, 1H); 4.71 (d, 1H); 5.11 (d, 1H); 6.99 (t, 1H); 7.35–7.5 (m, 5H); 8.3 (t, 1H); 11.3–11.8 (bs, 1H).

PREPARATION 20
Bis(1,1-dimethylethyl) 3-[[(1,1-dimethylethoxy)carbonyl]amino]-15-phenylmethoxy-25-methyl-22-phenylmethyl-14,16-dioxo-2,4,13,17,22,26-hexaazaheptacos-2-enedioate By following a procedure analogous to Preparation 16, using 2.55 g (4.4.10$^{-3}$ mol) of the product obtained according to Preparation 19 and 1.54 g (4.4. 10$^{-3}$ mol) of the compound obtained according to Preparation 5 as the starting materials, 3.5 g (yield=89%) of the expected product are obtained in the form of a yellow oil.

$^{1}$H NMR (CDCl$_3$): 1.04 (dd, 3H); 1.2–1.7 (m, 45H); 2.3–2.65 (m, 4H); 3.1–3.3 (m, 4H); 3.39 (td, 2H); 3.44 (d, 1H); 3.57 (d, 1H); 3.6–3.75 (m, 1H); 4.28 (s, 1H); 4.79 (s, 2H); 5.35–5.5 (bs, 1H); 6.85–7.1 (bs, 2H); 7.2–7.4 (m, 10H); 8.3 (t, 1H); 11.5 (s, 1H).

PREPARATION 21
Bis(1,1-dimethylethyl) 3-[[(1,1-dimethylethoxy)carbonyl]amino]-15-hydroxy-25-methyl-14,16-dioxo-2,4,13,17,22,26-hexaazaheptacos-2-enedioate By following a procedure analogous to Preparation 15, using 3.5 g (3.92.10$^{-3}$ mol) of the compound obtained according to Preparation 20 as the starting material, 2.4 g (yield=85%) of the expected product are obtained in the form of a yellow oil.

$^{1}$H NMR (CDCl$_3$): 1.15 (d, 3H); 1.2–1.8 (m, 46H); 2.55–2.75 (m, 4H); 3.2–3.45 (m, 6H); 3.65–3.8 (m, 1H); 4.42 (s, 1H); 4.75–4.9 (d, 1H); 7.2 (t, 1H); 7.4 (t, 1H); 8.3 (t, 1H); 11.5 (s, 1H).

EXAMPLE 5
N-[4-[[3-(Amino)butyl]amino]butyl]-2-hydroxy-N'-[8-[(aminoiminomethyl)amino]octyl]propanediamide tris (trifluoroacetate)

By following a procedure analogous to the method of Example 1, using 2.4 g (3.29.10$^{-3}$ mol) of the compound obtained according to Preparation 21 as the starting material, 2.27 g (yield=89.5%) of the expected product are obtained in the form of an amorphous white solid after purification by chromatography on RP18 silica gel using a water/acetonitrile/trifluoroacetic acid mixture (8/1.5/0.5) as the eluent.

$^{1}$H NMR (DMSO-d$_6$): 1.15–1.65 (m, 19H); 1.65–1.85 (m, 1H); 1.85–2 (m, 1H); 2.85–3.2 (m, 10H); 3.2–3.35 (m, 1H); 4.31 (s, 1H); 6.7–7.5 (bs, 3H); 7.59 (t, 1H); 7.8–8.05 (m, 6H); 8.45–8.7 (m, 2H).

$^{13}$C NMR (D$_2$O): 18.01; 23.65; 26.32; 26.49; 26.61; 28.60; 28.95; 29.04; 31.21; 39.20; 40.15; 41.97; 44.59; 46.09; 48.12; 73.14; 157.56; 171.15; 171.53.

PREPARATION 22
Bis(1,1-dimethylethyl) 3-[[(1,1-dimethylethoxy)carbonyl]amino]-13-methoxy-23-methyl-20-phenylmethyl-12,14-dioxo-2,4,11,15,20,24-hexaazapentacos-2-enedioate By following a procedure analogous to the method of Preparation 16, using 3 g (6.3.10$^{-3}$ mol) of 1-(1,1-dimethylethyl) 3-[[(1,1-dimethylethoxy)carbonyl]amino]-13-methoxy-12-oxo-2,4,11-triazatetradec-2-enedioate and 2.2 g (6.3.10$^{-3}$ mol) of the compound obtained according to Preparation 5 as the starting materials, 3.6 g (yield=68%/ of the expected product are obtained in the form of a yellow oil.

$^{1}$H NMR (CDCl$_3$): 1.05 (dd, 3H); 1.2–1.8 (m, 41H); 2.3–2.7 (m, 4H); 3.1–3.8 (m, 12H); 4.1 (s, 1H); 5.5 (m, 1H); 6.9 (m, 2H); 7.29 (m, 5H); 8.29 (t, 1H); 11.5 (s, 1H).

PREPARATION 23
Bis(1,1-dimethylethyl) 3-[[(1,1-dimethylethoxy)carbonyl]amino]-13-methoxy-23-methyl-12,14-dioxo-2,4,11,15,20,24-hexaazapentacos-2-enedioate hydrochloride A solution of 3.3 g (4.1.10$^{-3}$ mol) of the compound obtained according to Preparation 22 is prepared in 100 ml of ethanol, and 0.2 ml of concentrated hydrochloric acid and 300 mg of 10% palladium-on-charcoal are added. The mixture is hydrogenated at room temperature and at atmospheric pressure for 2 hours. The catalyst is filtered off and the filtrate is concentrated under reduced pressure to give 2.92 g (yield=94.8%1 of the expected product in the form of a white solid.

$^{1}$H NMR (CDCl$_3$): 1.1–2.3 (m, 44H); 2.8–3.6 (m, 11H), 3.4–3.6 (s, 3H); 4.4 (s, 1H); 4.9 (m, 1H); 7.6 (m, 1H); 7.9 (t, 1H); 9.3 (m, 1H); 9.9 (m, 1H); 11.4 (s, 1H).

EXAMPLE 6

N-[4-[[3-(Amino)butyl]amino]butyl]-N'-[6-[(aminoiminomethyl)amino]hexyl]-2-methoxypropanediamide tris(trifluoroacetate)

By following a procedure analogous to the method of Example 1, using 2.7 g ($3.6.10^{-3}$ mol) of the compound obtained according to Preparation 23 as the starting material, 2.11 g (yield=78%) of the expected product are obtained in the form of an amorphous solid after purification by chromatography on RP18 silica gel using a water/acetonitrile/trifluoroacetic acid mixture (8/1.5/0.5 v/v/v) as the eluent.

$^1$H NMR (DMSO-$d_6$): 1.2 (d, 3H); 1.4 (m, 12H); 1.75–1.95 (2m, 1H); 3.0 (m, 11H); 3.3 (s, 3H); 4.1 (s, 1H); 7.1 (bs, 3H); 7.6 (t, 1H); 8.0 (m, 4H); 8.6 (m, 2H).

$^{13}$C NMR ($D_2O$): 18.01; 23.68; 26.18; 26.29; 26.32; 28.55; 28.92; 31.21; 39.21; 39.99; 41.87; 44.60; 46.10; 48.11; 58.65; 82.43; 157.54; 165.65; 169.96.

PREPARATION 24

1-(1,1-Dimethylethyl) 16-methyl 3-[[(1,1-dimethylethoxy)carbonyl]amino]-15-methoxy-14-oxo-2,4,13-triazahexadec-2-enedioate By following a procedure analogous to the method of Preparation 18, using 3.5 g ($23.65.10^{-3}$ mol) of methyl 2-methoxypropanedioate and 7 g ($18.1.10^{-3}$ mol) of bis(1,1-dimethylethyl) [[(8-aminooctyl)imino]methylene]biscarbamate as the starting materials, 8.6 g (yield=95%) of the expected product are obtained in the form of a yellow oil.

$^1$H NMR (CDCl$_3$): 1.2–1.65 (m, 30H); 3.2–3.35 (m, 2H); 3.38 (td, 2H); 3.47 (s, 3H); 3.82 (s, 3H); 4.30 (s, 1H); 6.6 (t, 1H); 8.3 (t, 1H); 11.5 (s, 1H).

PREPARATION 25

1-(1,1-Dimethylethyl) 3-[[(1,1-dimethylethoxy)carbonyl]amino]-15-methoxy-14-oxo-2,4,13-triazahexadec-2-enedioate By following a procedure analogous to Preparation 7, using 8.6 g ($16.7.10^{-3}$ mol) of the compound obtained according to Preparation 24 as the starting material, 8.2 g (yield=98%) of the expected product are obtained in the form of an amorphous yellow solid.

$^1$H NMR (CDCl$_3$): 1.25–1.7 (m, 30H); 3.2–3.45 (m, 4H); 3.69 (s, 3H); 4.26 (s, 1H); 6.9–7.1 (bs, 1H); 8.25–8.45 (bs, 1H); 11.3–11.9 (bs, 1H).

PREPARATION 26

Bis(1,1-dimethylethyl) 3-[[(1,1-dimethylethoxy)carbonyl]amino]-15-methoxy-25-methyl-22-phenylmethyl-14,16-dioxo-2,4,13,17,22,26-hexaazaheptacos-2-enedioate By following a procedure analogous to Preparation 16, using 4 g ($8.10^{-3}$ mol) of the compound obtained according to Preparation 25 as the starting material, 4.8 g (yield=72%) of the expected product are obtained in the form of a light yellow oil.

$^1$H NMR (CDCl$_3$): 1.05 (dd, 3H); 1.2–1.8 (m, 45H); 2.3–2.7 (m, 4H); 3.1–3.3 (m, 4H); 3.3–3.6 (m, 7H); 3.6–3.75 (m, 1H); 4.09 (s, 1H); 5.35–5.55 (bs, 1H); 6.75–7 (m, 2H); 7.2–7.35 (m, 5H); 8.3 (t, 1H); 11.5 (s, 1H).

PREPARATION 27

Bis(1,1-dimethylethyl) 3-[[(1,1-dimethylethoxy)carbonyl]amino]-15-methoxy-25-methyl-14,16-dioxo-2,4,13,17,22,26-hexaazaheptacos-2-enedioate By following a procedure analogous to Preparation 23, using 4.8 g ($5.76.10^{-3}$ mol) of the compound obtained according to Preparation 26 as the starting material, 4.15 g (yield=97%) of the expected product are obtained in the form of an oil.

$^1$H NMR (CDCl$_3$): 1.15 (d, 3H); 1.25–1.8 (m, 45H); 1.9–2.1 (bs, 1H); 2.6–2.75 (m, 4H); 3.2–3.35 (m, 4H); 3.35–3.45 (m, 2H); 3.57 (s, 3H); 3.65–3.8 (m, 1H); 4.12 (s, 1H); 4.8–4.9 (bs, 1H); 6.85 (t, 1H); 7.2–7.35 (m, 1H); 8.3 (t, 1H); 11.5 (s, 1H).

EXAMPLE 7

N-[4-[[3-(Amino)butyl]amino]butyl]-2-methoxy-N'-[8-[(aminoiminomethyl)amino]octyl]propanediamide tris(trifluoroacetate)

By following a procedure analogous to the method of Example 1, using 4.15 g ($5.58.10^{-3}$ mol) of the compound obtained according to Preparation 27 as the starting material, 3.8 g (yield=86.5%) of the expected product are obtained in the form of an amorphous white solid.

$^1$H NMR (DMSO-$d_6$): 1.18 (d, 3H); 1.2–1.35 (m, 8H); 1.35–1.65 (m, 8H); 1.65–1.85 (m, 1H); 1.85–2 (m, 1H); 2.8–3.2 (m, 10H); 3.25–3.4 (m, 4H); 4.08 (s, 1H); 6.6–7.5 (bs, 3H); 7.62 (t, 1H); 7.9–8.1 (m, 6H); 8.5–8.7 (bs, 2H).

$^{13}$C NMR ($D_2O$): 18.01; 23.67; 26.33; 26.50; 26.63; 28.60; 28.94; 28.93; 29.01; 31.21; 39.18; 40.14; 41.97; 44.59; 46.09; 48.11; 58.68; 82.44; 157.54; 169.60; 169.97.

PREPARATION 28

1-(1,1-Dimethylethyl) 14-ethyl 13-fluoro-6-phenylmethyl-12-oxo-2,6,11-triazatetradecanedioate A solution of 1.3 g ($8.7.10^{-3}$ mol) of ethyl 2-fluoropropanedioate is prepared in 30 ml of dichloromethane and 3 ml of dimethylformamide, and 2.2 g ($13.5.10^{-3}$ mol) of 1,1-carbonyldiimidazole are added. The mixture is stirred for 3 hours at room temperature and a solution of 3 g ($8.7.10^{-3}$ mol) of the compound obtained according to Preparation 5 in 10 ml of dichloromethane is then added. Stirring is continued for 48 hours at room temperature. The reaction medium is concentrated under reduced pressure and purified by chromatography on silica gel using an ethyl acetate/cyclohexane mixture (6/4 v/v) as the eluent to give 2.3 g (yield=55.6%) of the expected product in the form of a yellow oil.

$^1$H NMR (CDCl$_3$): 1.04 (d, 3H); 1.2–1.7 (m, 18H); 2.3–2.5 (m, 2H); 2.5–2.65 (m, 2H); 3.4–3.8 (m, 5H); 4.25–4.4 (m, 2H); 5.25 (d, 2H); 6.7 (bs, 1H); 7.3 (m, 5H).

PREPARATION 29

1-(1,1-Dimethylethyl) 13-fluoro-6-phenylmethyl-12-oxo-2,6,11-triazatetradecanedioate By following a procedure analogous to Preparation 7, using 2.25 g ($4.7.10^{-3}$ mol) of the product obtained according to Preparation 28 as the starting material, 1.44 g (yield=68%) of the expected product are obtained in the form of a white powder.

M.p. =50° C.

$^1$H NMR (CDCl$_3$): 1.1 (d, 3H); 1.4–2.1 (m, 15H); 2.7–3.5 (m, 7H); 4.0–4.3 (m, 2H); 4.8 (m, 1H); 5.4 (m, 1H); 6.3–6.8 (m, 1H); 7.4 (m, 5H).

PREPARATION 30

Bis(1,1-dimethylethyl) 3-[[(1,1-dimethylethoxy)carbonyl]amino]-13-fluoro-23-methyl-20-phenylmethyl-12,14-dioxo-2,4,11,15,20,24-hexaazapentacos-2-enedioate By following a procedure analogous to the method of Preparation 16, using 670 mg ($1.5.10^{-3}$ mol) of the compound obtained according to Preparation 29 and 530 mg (1.5.10$^{-3}$ mol) of bis(1,1-dimethylethyl) [[(6-aminohexyl)imino]methylene]biscarbamate as the starting materials, 570 mg (yield=49%) of the expected product are obtained in the form of a light yellow oil.

$^1$H NMR (CDCl$_3$): 1.0–1.1 (d, 3H); 1.2–1.7 (m, 41H); 2.3–2.7 (m, 4H); 3.2–3.8 (m, 9H); 5.07–5.2 (dd, 1H); 6.8–7.1 (m, 2H); 7.2–7.4 (m, 5H); 8.29 (t, 1H); 11.5 (s, 1H).

PREPARATION 31

Bis(1,1-dimethylethyl) 3-[[(1,1-dimethylethoxy)carbonyl]amino]-13-fluoro-23-methyl-12,14-dioxo-2,4,11,15,20,24-hexaazapentacos-2-enedioate hydrochloride By following a procedure analogous to the method of Preparation 23, using 560 mg (0.7.10$^{-3}$ mol) of the product obtained according to Preparation 30 as the starting material, 484 mg (yield=93%) of the expected product are obtained in the form of a white solid.

$^1$H NMR (CDCl$_3$): 1.1–2.1 (m, 44H); 3.0–3.8 (m, 11H); 4.8 (m, 1H); 5.4–5.6 (d, 1H); 8 (m, 1H); 8.5 (m, 1H); 9.7 (m, 1H); 10.7 (m, 1H); 11.3 (s, 1H).

EXAMPLE 8

N-[4-[[3-(Amino)butyl]amino]butyl]-2-fluoro-N'-[6-[(aminoiminomethyl)amino]hexyl]propanediamide tris (trifluoroacetate)

By following a procedure analogous to the method of Example 1, using 460 mg (0.62.10$^{-3}$ mol) of the compound obtained according to Preparation 31 as the starting material, 350 mg (yield=67%) of the expected product are obtained in the form of an amorphous white solid.

$^1$H NMR (DMSO-d$_6$): 1.1 (d, 3H); 1.2–1.6 (m, 12H); 1.7–1.9 (2m, 2H); 2.8–3.2 (m, 10H); 3.27 (m, 1H); 5.1–5.28 (d, 1H); 7.1 (m, 4H); 7.6 (t, 1H); 7.95 (s, 3H); 8.35–8.65 (m, 4H).

$^{13}$C NMR (DMSO-d$_6$): 17.89; 22.83; 25.67; 25.81; 25.86; 28.34; 28.68; 30.40; 37.87; 38.45; 40.64; 43.17; 44.38; 46.43; 86.46; 156.51; 170.12; 170.14.

PREPARATION 32

Bis(1,1-dimethylethyl) 3-[[(1,1-dimethylethoxy)carbonyl]amino]-15-fluoro-25-methyl-22-phenylmethyl-14,16-dioxo-2,4,13,17,22,26-hexaazaheptacos-2-enedioate By following a procedure analogous to Preparation 16, using 670 mg (1.5.10$^{-3}$ mol) of the compound obtained according to Preparation 29 and 571 mg (1.5. 10$^{-3}$ mol) of bis(1,1-dimethylethyl) [[(8-aminooctyl)imino]methylene] biscarbamate as the starting materials,. 1 g (yield=83.3%) of the expected product is obtained in the form of a yellow oil.

$^1$H NMR (CDCl$_3$): 1.06 (d, 3H); 1.2–1.8 (m, 45H); 2.5 (m, 4H); 3.2–3.8 (m, 9H); 5.1–5.2 (d, 1H); 5.2 (m, 1H); 6.9 (m, 2H); 7.3 (m, 5H); 8.23 (t, 1H); 11.5 (s, 1H).

PREPARATION 33

Bis(1,1-dimethylethyl) 3-[[(1,1-dimethylethoxy)carbonyl]amino]-15-fluoro-25-methyl-14,16-dioxo-2,4,13,17,22,26-hexaazaheptacos-2-enedioate hydrochloride By following a procedure analogous to Preparation 23, using 1 g (1.2.10$^{-3}$ mol) of the compound obtained according to Preparation 32 as the starting material, 746 mg (yield=81%) of the expected product are obtained in the form of a hygroscopic white solid.

$^1$H NMR (CDCl$_3$): 1.1–2.1 (m, 48H); 2.8–3.5 (m, 9H); 3.6–3.8 (m, 2H); 4.9 (bs, 1H); 5.6 (d, 2H); 7.9 (bs, 1H); 8.5 (m, 1H); 11.4 (m, 1H).

EXAMPLE 9

N-[4-[[3-(Amino)butyl]amino]butyl]-2-fluoro-N'-[8-[(aminoiminomethyl)amino]octyl]propanediamide tris (trifluoroacetate)

By following a procedure analogous to the method of Example 1, using 740 mg (0.96.10$^{-3}$ mol) of the compound obtained according to Preparation 33 as the starting material, 400 mg (yield=54%) of the expected product are obtained in the form of an amorphous white solid.

$^1$H NMR (DMSO-d$_6$): 1.1–1.6 (m, 19H); 1.75–1.95 (2m, 2H); 2.8–3.2 (m, 10H); 3.3 (m, 1H); 5.12–5.28 (d, 1H); 7.1 (bs, 1H); 7.6 (t, 1H); 7.94 (s, 3H); 8.3–8.6 (m, 4H).

$^{13}$C NMR (D$_2$O): 18.01; 23.65; 26.19; 26.48; 26.57; 28.59; 28.88; 28.91; 28.94; 31.21; 39.30; 40.22; 41.97; 44.59; 46.10; 48.09; 87.27; 89.87; 156.81; 170.12; 170.14.

PREPARATION 34

1-(1,1-Dimethylethyl) 13-ethyl 3-methyl-6-phenylmethyl-12-oxo-2,6,11-triazatridecanedioate 7 g (20.10$^{-3}$ mol) of the compound obtained according to Preparation 5 are dissolved in 100 ml of anhydrous dichloromethane, 5.25 g (52.10$^{-3}$ mol) of triethylamine are added and 3.56 g (26.10$^{-3}$ mol) of ethoxalyl chloride are then added slowly, the mixture being cooled to 10° C. in a water bath. It is stirred for 15 min after the addition has ended and is then concentrated under reduced pressure. The residue is purified by chromatography on silica gel using a methylcyclohexane/ethyl acetate mixture (4/6, then 1/9 v/v) as the eluent to give 6.8 g (yield=75.7%) of the expected product in the form of a yellow oil.

$^1$H NMR (CDCl$_3$): 1.0 (d, 3H); 1.3–1.8 (m, 18H); 2.3–2.65 (m, 4H); 3.2–3.35 (m, 2H); 3.4 (d, 1H); 3.58 (d, 1H); 3.6–3.8 (m, 1H); 4.3 (q, 2H); 5.2–5.4 (bs, 1H); 7.2–7.5 (m, 6H).

PREPARATION 35

1-(1,1-Dimethylethyl) 3-methyl-6-phenylmethyl-12-oxo-2,6,11-triazatridecanedioate By following a procedure analogous to Preparation 7, using 6.8 g (15.14.10$^{-3}$ mol) of the compound obtained according to Preparation 34 as the starting material, 6.4 g (quantitative yield) of the expected product are obtained in the form of an amorphous white solid.

$^1$H NMR (CDCl$_3$): 1.1 (d, 3H); 1.3–1.9 (m, 15H); 2.5–3.45 (m, 8H); 3.5–3.7 (m, 1H); 5.3–5.6 (bs, 1H); 7.25–7.6 (m, 5H); 7.7–8 (bs, 1H).

PREPARATION 36

Bis(1,1-dimethylethyl) 3-[[(1,1-dimethylethoxy)carbonyl]amino]-22-methyl-19-phenylmethyl-12,13-dioxo-2,4,11,14,19,23-hexaazatetracos-2-enedioate By following a procedure analogous to Preparation 18, using 4 g (9.5.10$^{-3}$ mol) of the compound obtained according to Preparation 35 and 3.4 g (9.5. 10$^{-3}$ mol) of bis(1,1-dimethylethyl) [[(6-aminohexyl)-imino]methylene] biscarbamate as the starting materials, 1.46 g (yield=20%) of the expected product are obtained in the form of a yellow oil.

$^1$H NMR (CDCl$_3$): 1.05 (d, 3H); 1.3–1.8 (m, 41H); 2.3–2.6 (m, 4H); 3.1–3.35 (m, 4H); 3.40 (td, 1H); 3.45 (d, 1H); 3.6 (d, 1H); 3.6–3.8 (m, 1H); 5.3–5.5 (bs, 1H); 7.2–7.35 (m, 5H); 7.4–7.6 (m, 2H); 8.3 (t, 1H); 11.5 (s, 1H).

PREPARATION 37

Bis(1,1-dimethylethyl) 3-[[(1,1-dimethylethoxy)carbonyl]amino]-22-methyl-12,13-dioxo-2,4,11,14,19,23-hexaazatetracos-2-enedioate By following a procedure analogous to Preparation 15, using 1.46 g of the compound obtained according to Preparation 36 as the starting material, 1.25 g (yield=97.5%) of the expected product are obtained in the form of a yellow oil.

¹H NMR (CDCl₃): 1.2 (d, 3H); 1.3–1.8 (m, 41H); 2.6–2.8 (m, 4H); 3.25–3.85 (m, 8H); 4.85 (d, 1H); 7.45 (t, 1H); 7.85 (t, 1H); 8.3 (t, 1H); 11.5 (s, 1H).

EXAMPLE 10

N-[4-[[3-(Amino)butyl]amino]butyl]-N'-[6-[(aminoiminomethyl)amino]hexyl]ethanediamide tris (trifluoroacetate)

By following a procedure analogous to the method of Example 1, using 1.25 g of the compound obtained according to Preparation 37 as the starting material, 580 mg (yield=43%) of the expected product are obtained in the form of an amorphous white solid.

¹H NMR (DMSO-d₆): 1.2 (d, 3H); 1.25–1.65 (m, 12H); 1.65–1.85 (m, 1H); 1.85–2.0 (m, 1H); 2.8–3.2 (m, 10H); 3.2–3.4 (m, 1H); 6.8–7.5 (bs, 3H); 7.65 (t, 1H); 7.9–8.1 (bs, 4H); 8.5–8.7 (bs, 2H); 8.71 (t, 1H); 8.77 (t, 1H).

¹³C NMR (D₂O): 18.00; 23.77; 26.13; 26.23; 26.41; 28.54; 28.82; 31.21; 39.54; 40.31; 41.88; 44.61; 46.09; 48.12; 157.55; 161.65; 161.98.

PREPARATION 38

Bis(1,1-dimethylethyl) 3-[[(1,1-dimethylethoxy)carbonyl]amino]-24-methyl-21-phenylmethyl-14,15-dioxo2,4,13,16,21,25-hexaazahexacos-2-enedioate By following a procedure analogous to Preparation 18, using 2.73 g (6.47.10⁻³ mol) of the compound obtained according to Preparation 35 and 2.5 g (6.47.10⁻³ mol) of bis(1,1-dimethylethyl) [[(8-aminooctyl)imino]methylene] biscarbamate as the starting materials, 2 g (yield=39%) of the expected product are obtained in the form of a yellow oil.

¹H NMR (CDCl₃): 1.05 (d, 3H); 1.1–1.8 (m, 45H); 2.3–2.7 (m, 4H); 3.15–3.30 (m, 4H); 3.4 (td, 2H); 3.45 (d, 1H); 3.6 (d, 1H); 3.6–3.75 (m, 1H); 5.3–5.5 (bs, 1H); 7.2–7.35 (m, 5H); 7.35–7.6 (m, 2H); 8.3 (t, 1H); 11.5 (s, 1H).

PREPARATION 39

Bis(1,1-dimethylethyl) 3-[[(1,1-dimethylethoxy)carbonyl]amino]-24-methyl-14,15-dioxo-2,4,13,16,21,25-hexaazahexacos-2-enedioate By following a procedure analogous to Preparation 15, using 2 g (2.53.10⁻³ mol) of the compound obtained according to Preparation 38 as the starting material, 1.75 g (yield=99%) of the expected product are obtained in the form of a colorless oil.

¹H NMR (CDCl₃): 1.2 (dd, 3H); 1.2–1.8 (m, 45H); 2.45–2.9 (m, 4H); 3.1–3.8 (m, 8H); 4.7–4.85 (bs, 1H); 7.4–7.5 (bs, 1H); 7.7–7.85 (bs, 1H); 8.3 (t, 1H); 11.5 (s, 1H).

EXAMPLE 11

N-[4-[[3-(Amino)butyl]amino]butyl]-N'-[8-[(aminoiminomethyl)amino]octyl]ethanediamide tris (trifluoroacetate)

By following a procedure analogous to the method of Example 1, using 1.75 g (2.5.10⁻³ mol) of the compound obtained according to Preparation 39 as the starting material, 250 mg (yield=13.5%) of the expected product are obtained in the form of an amorphous white solid.

¹H NMR (DMSO-d₆): 1.2 (d, 3H); 1.2–1.6 (m, 16H); 1.6–1.8 (m, 1H); 1.8–2.0 (m, 1H); 2.8–3.2 (m, 10H); 3.2–3.35 (m, 1H); 6.7–7.4 (bs, 3H); 7.55 (t, 1H); 7.85–8.05 (bs, 4H); 8.4–8.6 (bs, 2H); 8.7 (t, 1H); 8.77 (t, 1H).

¹³C NMR (D₂O): 15.00; 20.77; 23.12; 23.51; 23.74; 5.60; 25.91; 25.94; 25.98; 28.20; 36.53; 37.45; 38.97; 1.60; 43.09; 45.11; 157.45; 161.55; 161.88.

PREPARATION 40

Bis(1,1-dimethylethyl) 3-[[(1,1-dimethylethoxy)carbonyl]amino]-24-methyl-21-phenylmethyl-12,15-dioxo-2,4,11,14,16,21,25-heptaazahexacos-2-enedioate 2 g (4.8.10⁻³ mol) of 1,1-dimethylethyl 13-amino-3-[[(1,1-dimethylethoxy)carbonyl]amino]-12-oxo-2,4,11-triazatridec-2-enoate are dissolved in 50 ml of dichloromethane, and 1.6 g (5.3.10⁻³ mol) of bis(4-nitrophenyl) carbonate are added in portions at room temperature. The mixture is stirred for 5 hours at room temperature and a solution of 1.68 g (4.8.10⁻³ mol) of the compound obtained according to Preparation 5 in 15 ml of dichloromethane is then added. The reaction medium is stirred at room temperature for 16 hours and then concentrated under reduced pressure. The residue is purified by chromatography on silica gel using an ethyl acetate/cyclohexane mixture (4/6 v/v) and then an ethyl acetate/ethanol mixture (9/1 v/v) as the eluent to give 2.59 g (yield=68%) of the expected product in the form of a yellow solid.

¹H NMR (CDCl₃): 1.0–1.1 (d, 3H); 1.2–1.8 (m, 41H); 2.3–2.7 (2m, 4H); 3.1–3.4 (m, 8H); 3.5–3.6 (m, 1H); 3.9 (m, 2H); 5.2 (m, 1H); 5.7 (m, 1H); 6.4 (m, 1H); 6.8 (m, 1H); 7.3 (m, 5H); 8.3 (t, 1H); 11.45 (s, 1H).

PREPARATION 41

Bis(1,1-dimethylethyl) 3-[[(1,1-dimethylethoxy)carbonyl]amino]-24-methyl-12,15-dioxo-2,4,11,14,16,21,25-heptaazahexacos-2-enedioate hydrochloride A solution of 2.52 g (3.2.10⁻³ mol) of the compound obtained according to Preparation 40 in 40 ml of ethanol is hydrogenated under atmospheric pressure in the presence of 200 mg of 10% palladium-on-charcoal and 0.1 ml of hydrochloric acid. After a reaction time of 5 hours, the catalyst is filtered off and the solution is concentrated under reduced pressure. The residue is taken up with water and dichloromethane and acidified to pH 2. After two extractions with water, the combined aqueous phases are lyophilized. The amorphous solid obtained (2.2 g) is treated without further purification in the next Preparation.

¹H NMR (CDCl₃): 1.0–1.1 (d, 3H); 1.15–1.7 (m, 39H); 1.8 (m, 1H); 2.1 (m, 1H); 2.8–3.1 (m, 9H); 3.2–3.4 (2m, 2H); 3.6 (s, 2H); 7.3 (m, 2H); 8.2 (t, 2H); 7.8 (t, 1H); 9 (m, 1H); 11 (s, 1H).

EXAMPLE 12

N-[4-[[3-(Amino)butyl]amino]butyl]-N'-[[[6-[(aminoiminomethyl)amino]hexyl]amino]carbonyl]methyl] urea tris(trifluoroacetate)

By following a procedure analogous to the method of Example 1, using 2.2 g of the compound obtained according to Preparation 41 as the starting material, 1 g (yield=43%) of the expected product is obtained in the form of an amorphous white solid.

¹H NMR (DMSO-d₆): 1.1–1.65 (m, 15H); 1.7 (m, 1H); 1.9 (m, 1H); 3.0 (m, 10H); 3.3 (m, 1H); 3.6 (s, 2H); 4.5–5.5 (bs, 3H); 6.0–6.4 (m, 2H); 6.9–7.5 (m, 2H); 7.6 (t, 1H); 7.8 (t, 1H); 8 (s, 2H); 8.6 (m, 2H).

¹³C NMR (D₂O): 18.01; 23.69; 26.20; 26.31; 27.20; 28.56; 29.02; 31.22; 39.85; 39.95; 41.87; 43.98; 44.59; 46.10; 48.26; 157.90; 161.07; 173.72.

PREPARATION 42

1,1-Dimethylethyl (2-hydroxy-1(R)-methylethyl)carbamate

A solution of 24.3 g (0.323 mol) of 2(R)-aminopropanol is prepared in 450 ml of tetrahydrofuran and 8 ml of water. 32.6 g (0.323 mol) of triethylamine are added and a solution of 70.5 g (0.323 mol) of ditertbutyl dicarbonate (i.e. O[COC(CH$_3$)$_3$]$_2$) in 150 ml of tetrahydrofuran is then added slowly. The reaction medium is stirred for 1 hour at room temperature and then concentrated under reduced pressure. The oily residue is taken up with 400 ml of ethyl ether and washed with 2 times 100 ml of a 0.1N solution of hydrochloric acid containing sodium chloride and then with a solution of sodium bicarbonate. The organic phase is dried over magnesium sulfate and concentrated under reduced pressure. The residue is taken up with 200 ml of cyclohexane and crystallized. The crude product is finally recrystallized from 350 ml of cyclohexane to give 49.3 g (yield=87%) of the expected product in the form of white crystals.

M.p. =60° C.

$[\alpha]_D^{22}$=+12.1° (c=1.00; CHCl$_3$).

PREPARATION 43

1,1-Dimethylethyl [2-(methylsulfonyloxy)-1(R)-methylethyl]carbamate 55 g (0.314 mol) of the product obtained according to Preparation 42 are dissolved in 600 ml dichloromethane, and 90 g (0.89 mol) of triethylamine are added. The mixture is cooled to −5° C. and a solution of 51 g (0.445 mol) of methanesulfonyl chloride in 100 ml of dichloromethane is added slowly. The mixture is then allowed to return to room temperature and stirred for 15 hours. The reaction medium is then poured into 200 ml of iced water. The organic phase is washed with a solution of sodium chloride and then dried over magnesium sulfate and concentrated under reduced pressure to give 79 g (quantitative yield) of the expected crude product in the form of orange crystals, which are used as such in the next operation. The product can be purified by recrystallization from heptane.

M.p. =76° C.

$[\alpha]_D^{23}$=+29.7° (c=1.02; CHCl$_3$).

PREPARATION 44

1,1-Dimethylethyl (2-cyano-1(R)-methylethyl)carbamate 79 g (0.31 mol) of the compound obtained according to Preparation 43 are dissolved in 600 ml of dimethyl sulfoxide, and 40.5 g (0.62 mol) of potassium cyanide are added. The reaction medium is then stirred at 50° C. for 15 hours. It is cooled and hydrolyzed in 600 ml of iced water. It is extracted with 4 times 500 ml of ethyl ether and the organic phases are dried over magnesium sulfate. After concentration under reduced pressure, the crude product is purified by chromatography on silica gel using a methylcyclohexane/ethyl acetate mixture (8/2 v/v) as the eluent to give 42 g of an oil, which crystallizes. After recrystallization from a mixture of methylcyclohexane and isopropyl ether, 33 g (yield=57%) of the expected product are obtained in the form of white crystals.

M.p. =70° C.

$[\alpha]_D^{23}$=+93.2° (c=1.00; CHCl$_3$).

PREPARATION 45

1,1-Dimethylethyl (3-amino-1(R)-methylpropyl)carbamate

A solution of 23.64 g (0.128 mol) of the compound obtained according to Preparation 44 is prepared in 500 ml of ethanol, and 10 ml of a 1N solution of NaOH and 7 g of Raney nickel are added. The mixture is stirred under a hydrogen pressure of 20.10$^5$ pascals for 48 hours. After the catalyst has been filtered off, the filtrate is neutralized by the addition of 1N hydrochloric acid and concentrated under reduced pressure. The residue is purified by chromatography on silica gel using a methylcyclohexane/ethyl acetate/aqueous ammonia mixture (7.5/2/0.5 v/v) as the eluent to give 22.1 g (yield=91.5%) of the expected pure product, which crystallizes.

M.p. =73° C.

$[\alpha]_D^{23.5}$=+12.0° (c=1.00; CHCl$_3$).

PREPARATION 46

1,1-Dimethylethyl [3-(phenylmethylamino)-1(R)-methylpropyl]carbamate

A solution of 22.1 g (0.117 mol) of the compound obtained according to Preparation 45 is prepared in 300 ml of ethyl ether, and 20 g of a 3 Å molecular sieve and then 12.47 g (0.117 mol) of benzaldehyde are added. The mixture is stirred for 15 hours at room temperature, the molecular sieve is then filtered off and the filtrate is concentrated under reduced pressure to give 32.6 g of the intermediate imine, which is dissolved in 350 ml of ethanol. 6.7 g (0.177 mol) of sodium borohydride are added to the solution in portions, the temperature being kept at about 10° C. The mixture is subsequently stirred for 3 hours and then concentrated under reduced pressure. The residue is taken up with 500 ml of ethyl ether and the organic phase is washed with water, dried over magnesium sulfate and concentrated under reduced pressure. After recrystallization of the residue from cyclohexane, 32.5 g (yield=98%) of the expected product are obtained in the form of yellow crystals.

M.p. =79° C.

$[\alpha]_D^{23}$=−5.2° (c=2.00; CHCl$_3$).

PREPARATION 47

1,1-Dimethylethyl 9-cyano-3(R)-methyl-6-phenylmethyl-2,6-diazanonanoate

A solution of 32 g (0.115 mol) of the compound obtained according to Preparation 46 and 18.2 g (0.175 mol) of 4-chlorobutyronitrile is prepared in 300 ml of butanol. 14.6 g (0.138 mol) of sodium carbonate and 4.8 g of potassium iodide are added and the mixture is refluxed for 15 hours, with stirring. It is concentrated under reduced pressure and the residue is purified by chromatography on silica gel using a methylcyclohexane/ethyl acetate mixture (8/2, then 1/1 v/v) as the eluent to give 39 g (yield=98%) of the expected product in the form of a very viscous yellow oil.

$[\alpha]_D^{23}$=−6.9° (c=2.00; CHCl$_3$).

PREPARATION 48

1,1-Dimethylethyl 10-amino-3(R)-methyl-6-phenylmethyl-2,6-diazadecanoate

By following a procedure analogous to Preparation 45, operating under a hydrogen pressure of 3.5.10$^{-5}$ pascals and using 32.8 g (95.10$^{-3}$ mol) of the compound obtained according to Preparation 45 as the starting material, 33 g (yield=99%) of the expected product, are obtained in the form of a viscous colorless oil.

$[\alpha]_D^{23}$=−1.9° (c=1.00; CHCl$_3$).

$^1$H NMR (CDCl$_3$): 1.04 (d, 3H); 1.35–1.8 (m, 17H); 2.3–2.5 (m, 4H); 2.64 (t, 2H); 3.44 (d, 1H); 3.61 (d, 1H); 3.62–3.8 (m, 1H); 5.6–5.8 (bs, 1H); 7.2–7.35 (m, 5H).

PREPARATION 49

1,1-Dimethylethyl 10-amino-3(S)-methyl-6-phenylmethyl-2,6-diazadecanoate

The expected chiral derivative having the S configuration is obtained by a sequence of reactions analogous to Preparations 42 to 48, using 2(S)-amino-propanol as the starting material.

$[\alpha]_D^{23}$=+1.6° (c=1.20; CHCl₃).

PREPARATION 50

1,1-Dimethylethyl 3(R)-methyl-10-[2,4-dioxooxazolidin-3-yl]-6-phenylmethyl-2,6-diazadecanoate By following a procedure analogous to Preparation 10, using 1.8 g ($5.15.10^{-3}$ mol) of the compound obtained according to Preparation 48 as the starting material, the expected product is obtained in the form of white crystals with a yield of 90%.

M.p. =62° C.

$[\alpha]_D^{22}$=−1° (c=1.00; CHCl₃).

PREPARATION 51

1,1-Dimethylethyl 3(S)-methyl-10-[2,4-dioxooxazolidin-3-yl]-6-phenylmethyl-2,6-diazadecanoate By a method identical to Preparation 50, using the compound of Preparation 49 as the starting material, the expected product is obtained in the form of a colorless oil.

$[\alpha]_D^{22}$=+0.5° (c=1.00; CHCl₃).

¹H NMR (CDCl₃): 1.05 (d, 3H); 1.35–1.65 (m, 15H); 2.35–2.65 (m, 4H); 3.4–3.75 (m, 5H); 4.67 (s, 2H); 5.2–5.4 (bs, 1H); 7.2–7.4 (m, 5H).

PREPARATION 52

1-(1,1-Dimethylethyl) 3(R)-methyl-6-phenylmethyl-13-oxa-12-oxo-2,6,11-triazapentanedioate By following a procedure analogous to Preparation 11, using 2 g ($4.6.10^{-3}$ mol) of the compound obtained according to Preparation 50 as the starting material, 2.1 g (yield=99%) of the expected product are obtained in the form of amorphous white crystals.

$[\alpha]_D^{22}$=−3.9° (c=1.00; CHCl₃).

¹H NMR (CDCl₃): 1.17 (d, 3H); 1.25–2.1 (m, 15H); 2.35–3.3 (m, 8H); 3.45–3.7 (m, 1H); 4–4.35 (m, 2H); 4.8–5.2 (m, 1H); 7.15–7.8 (m, 6H); 12.1–12.7 (bs, 1H).

PREPARATION 53

1-(1,1-Dimethylethyl) 3(S)-methyl-6-phenylmethyl-13-oxa-12-oxo-2,6,11-triazapentanedioate By following a procedure analogous to Preparation 52, using the compound obtained according to Preparation 51 as the starting material, the expected product is obtained in the form of an amorphous white solid.

$[\alpha]_D^{22}$=+6.0° (c=0.41; CHCl₃).

PREPARATION 54

Bis(1,1-dimethylethyl) 3-[[(1,1-dimethylethoxy)carbonyl]amino]-24(R)-methyl-21-phenylmethyl-14-oxa-12,15-dioxo-2,4,11,16,21,25-hexaazahexacos-2-enedioate By following a procedure analogous to the method of Preparation 16, using 2.08 g ($4.61.10^{-3}$ mol) of the compound obtained in Preparation 52 as the starting material, 3.6 g (yield=99%) of the expected product are obtained in the form of a colorless oil.

$[\alpha]_D^{22}$=−2.3° (c=1.00; CHCl₃).

¹H NMR (CDCl₃): 1.01 (d, 3H); 1.3–1.8 (m, 41H); 2.3–2.5 (m, 3H); 2.5–2.65 (m, 1H); 3.05–3.2 (m, 2H); 3.2–3.3 (m, 2H); 3.35–3.5 (m, 3H); 3.6 (d, 1H); 3.65–3.8 (m, 1H); 4.5 (s, 2H); 5.35–5.6 (m, 2H); 6.25–6.4 (bs, 1H); 7.2–7.35 (m, 5H); 8.3 (t, 1H); 11.5 (s, 1H).

PREPARATION 55

Bis(1,1-dimethylethyl) 3-[[(1,1-dimethylethoxy)carbonyl]amino]-24(S)-methyl-21-phenylmethyl-14-oxa-12,15-dioxo-2,4,11,16,21,25-hexaazahexacos-2-enedioate By following a procedure analogous to Preparation 54, using 1.56 g of the compound obtained according to Preparation 53 as the starting material, 2.02 g (yield=74%) of the expected product are obtained in the form of a colorless oil.

$[\alpha]_D^{22}$=+1.8° (c=1.00; CHCl₃).

PREPARATION 56

Bis(1,1-dimethylethyl) 3-[[(1,1-dimethylethoxy)carbonyl]amino]-24(R)-methyl-14-oxa-12,15-dioxo-2,4,11,16,21,25-hexaazahexacos-2-enedioate By following a procedure analogous to Preparation 15, using 3.6 g ($4.5.10^{-3}$ mol) of the compound, obtained according to Preparation 54 as the starting material, 3.2 g (yield=99%) of the expected product are obtained in the form of a light yellow oil.

$[\alpha]_D^{23}$=+29.7° (c=1.02; CHCl₃). ¹H NMR (CDCl₃): 1.18 (d, 3H); 1.25–1.95 (m, 42H); 2.6–2.8 (m, 4H); 3.1–3.45 (m, 6H); 3.7–3.9 (m, 1H); 4.54 (s, 2H); 4.65–4.8 (bs, 1H); 5.8–6.1 (bs, 1H); 6.4–6.6 (bs, 1H); 8.3 (t, 1H); 11.5 (s, 1H).

PREPARATION 57

Bis(1,1-dimethylethyl) 3-[[(1,1-dimethylethoxy)carbonyl]amino]-24(S)-methyl-14-oxa-12,15-dioxo-2,4,11,16,21,25-hexaazahexacos-2-enedioate By following a procedure analogous to Preparation 56, using 2.0 g ($2.5.10^{-2}$ mol) of the compound obtained in Preparation 55 as the starting material, the expected product is obtained in the form of a yellow oil.

$[\alpha]_D^{22}$=+5.8° (c=1.00; CHCl₃).

EXAMPLE 13

2-[[[4-[[3(R)-(Amino)butyl]amino]butyl]amino]carbonyloxy]-N-[6-[(aminoiminomethyl)amino]hexyl]acetamide tris(trifluoroacetate)

By following a procedure analogous to the method of Example 1, using 3.2 g ($4.56.10^{-3}$ mol) of the compound obtained according to Preparation 56 as the starting material, 2.48 g (yield=73%) of the expected product are obtained in the form of an amorphous white solid.

$[\alpha]_D^{22}$=+1.1° (c=2.00; CHCl₃).

¹H NMR (DMSO-d₆): 1.18 (d, 3H); 1.25–1.65 (m, 12H); 1.65–1.85 (m, 1H); 1.85–2.0 (m, 1H); 2.85–3.15 (m, 10H); 3.2–3.35 (m, 1H); 4.33 (s, 2H); 6.8–7.3 (bs, 3H); 7.32 (t, 1H); 7.62 (t, 1H); 7.86 (t, 1H); 7.9–8.05 (bs, 4H); 8.5–8.7 (bs, 2H).

¹³C NMR (D₂O): 18.01; 23.64; 26.19; 26.28; 26.76; 28.56; 28.93; 31.21; 39.77; 40.58; 41.87; 44.60; 46.10; 48.21; 63.75; 157.55; 157.89; 171.44.

EXAMPLE 14

2-[[[4-[[3(S)-(Amino)butyl]amino]butyl]amino]carbonyloxy]-N-[6-[(aminoiminomethyl)amino]hexyl]acetamide tris(trifluoroacetate)

By following a procedure analogous to Example 13, using 1.75 g ($2.5.10^{-3}$ mol) of the compound obtained according to Preparation 57 as the starting material, 1.5 g (yield=82%) of the expected product are obtained in the form of an amorphous solid.

$[\alpha]_D^{22}$=−0.95° (c=2.00; CH₃OH).

PREPARATION 58

Bis(1,1-dimethylethyl) 3-[[(1,1-dimethylethoxy)carbonyl]amino]-23(R)-methyl-12,14-dioxo-20-phenylmethyl-2,4,11,15,20,24-hexaazapentacos-2-enedioate By following a procedure analogous to Preparation 18, using 4.88 g ($11.10^{-3}$ mol) of the compound obtained according to Preparation 7 and 2.75 g (7.88. $10^{-3}$ mol) of the compound obtained in Preparation 48 as the starting materials, 4.9 g (yield=80%) of the expected product are obtained in the form of a viscous oil.

$[\alpha]_D^{23}$=−4.1° (c=1.00; CHCl$_3$).

$^1$H NMR (CDCl$_3$): 1.02 (d, 3H); 1.25–1.85 (m, 41H); 2.25–2.7 (m, 4H); 3.05–3.8 (m, 11H); 5.2–5.4 (bs, 1H); 7–7.15 (bs, 1H); 7.15–7.4 (m, 6H); 8.3 (t, 1H); 11.5 (s, 1H).

PREPARATION 59

Bis(1,1-dimethylethyl) 3-[[(1,1-dimethylethoxy)carbonyl]amino]-23(R)-methyl-12,14-dioxo-2,4,11,15,20,24-hexaazapentacos-2-enedioate By following a procedure analogous to Preparation 15, using 4.9 g (6.32.10$^{-3}$ mol of the compound obtained according to Preparation 58 as the starting material, 4.32 g (yield=99%) of the expected product are obtained in the form of an oil.

$[\alpha]_D^{23}$=−2.8° (c=1.00; CHCl$_3$).

$^1$H NMR (CDCl$_3$): 1.2 (d, 3H); 1.25–2.0 (m, 42H); 2.6–2.8 (m, 4H); 3.16 (s, 2H); 3.2–3.55 (m, 6H); 3.6–3.85 (m, 1H); 4.75–4.95 (bs, 1H); 7.1–7.35 (bs, 1H); 7.65–7.8 (bs, 1H); 8.3 (t, 1H); 11.5 (s, 1H).

EXAMPLE 15

N-[4-[[3(R)-(Amino)butyl]amino]butyl]-N'-[6-[(aminoiminomethyl)amino]hexyl]propanediamide tris (trifluoroacetate)

By following a procedure analogous to the method of Example 1, using 4.3 g (6.27.10$^{-3}$ mol) of the compound obtained according to Preparation 59 as the starting material, 2.1 g (yield=46%) of the expected product are obtained in the form of a transparent amorphous solid after purification by chromatography on RP18 silica gel using a water/acetonitrile/trifluoroacetic acid mixture (8/1/1 v/v) as the eluent.

$[\alpha]_D^{23}$=+1.1° (c=1.00; CHCl$_3$).

$^1$H NMR (DMSO-d$_6$): 1.2 (d, 3H); 1.2–1.65 (m, 12H); 1.65–1.85 (m, 1H); 1.85–2 (m, 1H); 2.8–3.15 (m, 12H); 3.2–3.35 (m, 1H); 6.7–7.5 (bs, 3H); 7.62 (t, 1H); 7.7–8.2 (m, 6H); 8.3–8.8 (bs, 2H).

$^{13}$C NMR (D$_2$O): 18.02; 23.71; 26.23; 26.35; 28.56; 28.74; 28.84; 31.23; 39.50; 40.31; 41.88; 44.30; 44.61; 46.10; 48.15; 115.25; 119.11; 158.30; 170.02; 170.34.

The immunosuppressive activity of the products according to the invention was demonstrated with the aid of a test for graft-versus-host reaction. B6D2F1 male mice (C57B1/6×DBA/2 first generation hybrids) are immunosuppressed by means of an intraperitoneal (i.p.) injection of cyclophosphamide. After three days (day 0 of the experiment: D0), they receive 4×10$^7$ C57B1/6 mouse splenocytes by intravenous administration. The animals are then divided into groups of at least 8 and receive a daily treatment from D1 to D5 and from D7 to D10 by i.p. administration. The control group receives the vehicle only. The mortality is followed up to D60. The results, expressed as the mean value of the survival in days at the indicated dose, are collated in Table I, in which the values given are significant according to the Logrank test (probability less than or equal to 5%). For purposes of comparison, Table I also indicates the values obtained with the known products of the prior art: 15-deoxyspergualin (15-DSG), cyclosporin A, which is currently the reference immunosuppressant used in therapeutics, and the product of Example 1 described in EP-A-0 105 193. This comparison shows that the products according to the invention are up to 100 times more active than the known products of the prior art. In particular, the products according to the invention have a significant activity as from 0.3 mg/kg (lowest dose tested), where as the comparative product of Example 1 of EP-A-0 105 193 only has a significant activity as from 1 mg/kg and cyclosporin A as from 25 mg/kg.

Furthermore, the solution stability of the compounds according to the invention is markedly greater than that of the known products of the prior art, especially 15-deoxyspergualin.

The products according to the invention are useful in therapeutics as curative or preventive immunosuppressants, especially in preventing the rejection of vascularized or non-vascularized allogenic or xenogenic organs or the graft-versus-host reaction following a vascularized or non-vascularized graft, in treating genetically defined or acquired autoimmune diseases (for example systemic lupus erythematosus, multiple sclerosis, rheumatoid polyarthritis) or chronic inflammatory diseases, for example articular rheumatism, as well as in any pathological condition where an immune disorder appears to be the cause or factor responsible for maintaining a degraded clinical state.

The products according to the invention can also be administered in combination with cytotoxic anticancer drugs in order to limit their side-effects, and in combination with the administration of products of biotechnological origin, especially recombinant cytokinins or monoclonal and polyclonal antibodies, in order to reduce the appearance of the protective antibodies produced by the patient.

The products according to the invention can be used in the curative treatment of parasitosis, in particular in the case of malaria.

The products according to the invention can be administered orally, by injection (especially intra-muscular or intravenous injection), topically (especially in the form of a cream for local application, or eye drops), transdermally, rectally in the form of a suppository, or by inhalation.

The products according to the invention are also useful as pharmacological reagents, especially in the study of autoimmune diseases.

In Table I, all the products cited from the Examples according to the invention are in the form of the tris (trifluoroacetate).

TABLE I $$H_2N-\underset{NH}{\overset{NH}{C}}-NH-(CH_2)_n-NH-\underset{O}{\overset{\|}{C}}-A-\underset{O}{\overset{\|}{C}}-NH-(CH_2)_4-NH-(CH_2)_2-\overset{*}{C}H(CH_3)-NH_2 \quad (I)$$

| Example | A | n | Chirality | Activity Dose (mg/kg) | Survival (days) |
|---|---|---|---|---|---|
| 1 | —CH₂— | 6 | racemate | 3 | 60 |
| 2 | —CH₂—O— | 6 | racemate | 0.3 | 53 |
| 3 | —CH₂— | 8 | racemate | 3 | 57 |
| 4 | —CH(OH)— | 6 | mixture of diastereoisomers | 3 | 60 |
| 5 | —CH(OH)— | 8 | mixture of diastereoisomers | 3 | 60 |
| 6 | —CH(OCH₃)— | 6 | mixture of diastereoisomers | 3 | 58 |
| 7 | —CH(OCH₃)— | 8 | mixture of diastereoisomers | — | — |
| 8 | —CHF— | 6 | mixture of diastereoisomers | — | — |
| 9 | —CHF— | 8 | mixture of diastereoisomers | 3 | 60 |
| 10 | single bond | 6 | racemate | 0.3 | 38 |
| 11 | single bond | 8 | racemate | 3 | 60 |
| 12 | —CH₂—NH— | 6 | racemate | 1 | 56 |
| 13 | —CH₂—O— | 6 | chiral (R form) | 0.3 | 60 |
| 15 | —CH₂— | 6 | chiral (R form) | — | — |
| 15-DSG | | | | 1 | 43 |
| cyclosporin A | | | | 25 | 36 |
| Ex. 1 of EP-A-0105193 | | | | 1 | 32 |

What is claimed is:

1. A 15-deoxy-spergualin analog selected from the group consisting of:

(i) the a compound of the formula

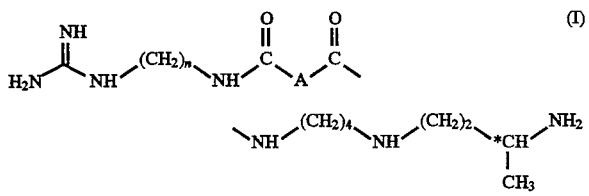

(I)

in which:

A is a single bond, a group —CH₂—, a group —CH₂O—, a group —CH₂NH—, a group —CH(OH)—, a group —CHF— or a group —CH(OCH₃)—, and n is equal to 6 or 8; and (ii) its their addition salt.

2. A compound according to claim 1 in which A is CH₂.

3. A compound according to claim 1 in which *C is a carbon having the (R) or (R,S) configuration.

4. A therapeutic composition which contains, in association with a physiologically acceptable excipient, at least one compound according to claim 3.

5. A therapeutic composition which contains, in association with a physiologically acceptable excipient, at least one compound according to claim 1.

6. A therapeutic composition according to claim 5 in which A is —CH₂— or —CH₂O—.

7. An intermediate useful for the synthesis of a compound of formula I according to claim 1, which is selected from the group consisting of the compounds of the formula $$R_1-\underset{R_1}{\overset{N}{\underset{\|}{C}}}-NH-(CH_2)_n-NH-\underset{O}{\overset{\|}{C}}-A-\underset{O}{\overset{\|}{C}}-NH-(CH_2)_4-\underset{R_2}{N}-(CH_2)_2-\overset{*}{C}H(CH_3)-NH-R_3 \quad (II)$$

in which:

A is a single bond, a group CH$_2$, a group CHF, a group CH(OCH$_3$), a group CH(OH), a group CH(OCH$_2$C$_6$H$_5$), a group CH$_2$O or a group CH$_2$NH, n is equal to 6 or 8, and R$_1$, R$_2$ and R$_3$, which are identical or different, are each an amino-protecting group of the alkoxycarbonyl, benzyloxycarbonyl or benzyl type.

8. A compound according to claim 1 in which A is —CH$_2$O—.

9. A compound according to claim 1 in which A is a bond, —CHF—, —CH(OCH$_3$)—, —CH(OH)— or —CH$_2$—NH—.

10. 2-[[[4-[[3-(Amino)butyl]amino]butyl]amino] carbonyloxy]-N-[6-[(aminoiminomethyl)amino]hexyl] acetamide tris(trifluoroacetate).

11. A therapeutic composition which contains, in association with a physiologically acceptable excipient, at least; one compound according to claim 10.

12. 2-[[[4-[[3(R)-(Amino)butyl]amino]butyl]amino] carbonyloxy]-N-[6-[(aminoiminomethyl)amino]hexyl] acetamide tris(trifluoroacetate).

13. A therapeutic composition which contains, in association with a physiologically acceptable excipient, at least one compound according to claim 12.

* * * * *

UNITED STATES PATENT AND TRADEMARK OFFICE
Certificate

Patent No. 5,637,613                                       Patented: June 10, 1997

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Patrice Renaut; Luc Lebreton; Patrick Dutartre; Soth Samreth; and Philippe Andre Derrepas, deceased.

Signed and Sealed this Twenty-Ninth Day of February, 2000.

GARY GEIST
*Supervisory Patent Examiner*
Art Unit 1621